(12) United States Patent
Chen et al.

(10) Patent No.: US 11,560,367 B2
(45) Date of Patent: Jan. 24, 2023

(54) PYRROLIDINONES AND A PROCESS TO PREPARE THEM

(71) Applicant: FMC Corporation, Philadelphia, PA (US)

(72) Inventors: Yuzhong Chen, Wilmington, DE (US); Rafael Shapiro, Wilmington, DE (US)

(73) Assignee: FMC Corporation, Philadelphia, PA (US)

( * ) Notice: Subject to any disclaimer, the term of this patent is extended or adjusted under 35 U.S.C. 154(b) by 0 days.

(21) Appl. No.: 17/127,058

(22) Filed: Dec. 18, 2020

(65) Prior Publication Data

US 2021/0107890 A1  Apr. 15, 2021

Related U.S. Application Data

(63) Continuation of application No. 16/495,717, filed as application No. PCT/US2018/022835 on Mar. 16, 2018, now Pat. No. 10,875,838.
(Continued)

(51) Int. Cl.
  C07D 401/04  (2006.01)
  C07D 207/16  (2006.01)

(52) U.S. Cl.
  CPC ......... *C07D 401/04* (2013.01); *C07D 207/16* (2013.01)

(58) Field of Classification Search
  CPC .................. C07D 401/04; C07D 207/16
  See application file for complete search history.

(56) References Cited

U.S. PATENT DOCUMENTS 3,741,989 A 6/1973 Zaugg
3,959,481 A 5/1976 Davis et al.
(Continued)

FOREIGN PATENT DOCUMENTS

CN 102531918 10/2013
DE 1262277 3/1968
(Continued)

OTHER PUBLICATIONS

Murata et al.; "Oxidation of N-Acyl-Pyrrolidines and -Piperidines with Iron(II)-Hydrogen Peroxide and an Iron Complex-Molecular Oxygen"; J Chem. Soc. Perkin Trans.; 1987; 1259-1262 (XP055297105).
(Continued)

*Primary Examiner* — Timothy R Rozof
(74) *Attorney, Agent, or Firm* — Reed A Coats; FMC Corporation

(57) ABSTRACT

This application is directed to a compound of Formula II Also disclosed is a process for preparing a compound of Formula II comprising using the compounds of Formulae IV and V Also disclosed is a method for preparing a compound of Formula I comprising contacting a compound of Formula II with a compound of a compound of Formula VI wherein $A^1, A^2, A^3, R^1, R^2, R^{3a}, R^{3b}, R^4, B^1, B^2$ and $B^3$, are as defined in the disclosure.

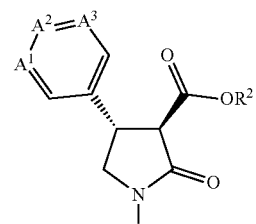

II

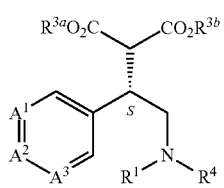

IV

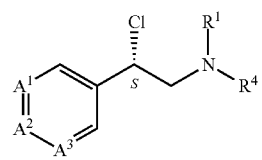

V

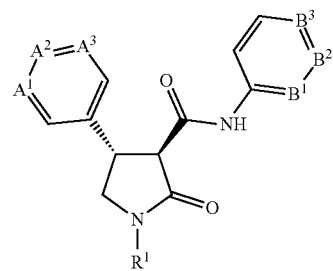

I

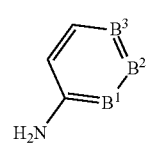

VI

12 Claims, No Drawings

Related U.S. Application Data

(60) Provisional application No. 62/474,206, filed on Mar. 21, 2017.

(56) References Cited

U.S. PATENT DOCUMENTS

| | | | |
|---|---|---|---|
| 4,046,898 | A | 9/1977 | Shaw |
| 4,594,094 | A | 6/1986 | Kollmeyer |
| 4,874,422 | A | 10/1989 | Woolard |
| 5,196,534 | A | 3/1993 | Whitehead et al. |
| 5,856,273 | A | 1/1999 | Kay et al. |
| 7,205,318 | B2 | 4/2007 | Qiao et al. |
| 7,355,053 | B2 | 4/2008 | Reinhard et al. |
| 7,375,232 | B2 | 5/2008 | Clark et al. |
| 8,293,926 | B2 | 10/2012 | Yasuoka et al. |
| 8,461,202 | B2 | 6/2013 | Sancho Sanz et al. |
| 8,575,154 | B2 | 11/2013 | Kori et al. |
| 8,946,216 | B2 | 2/2015 | Deng et al. |
| 9,119,397 | B2 | 9/2015 | Yerkes et al. |
| 9,446,995 | B2 | 9/2016 | Chong |
| 9,737,073 | B2 | 8/2017 | Gifford et al. |
| 9,944,602 | B2 | 4/2018 | Satterfield et al. |
| 9,969,728 | B2 | 5/2018 | Defays et al. |
| 10,227,286 | B2 | 3/2019 | Satterfield |
| 10,294,202 | B2 | 5/2019 | Satterfield et al. |
| 10,405,547 | B2 | 9/2019 | Satterfield et al. |
| 10,442,807 | B2 * | 10/2019 | Campbell ............ C07D 207/26 |
| 10,654,804 | B2 | 5/2020 | Satterfield et al. |
| 10,875,838 | B2 * | 12/2020 | Chen ................... A01N 43/36 |
| 11,178,873 | B2 | 11/2021 | Satterfield et al. |
| 2003/0176712 | A1 | 9/2003 | Abe et al. |
| 2004/0242671 | A1 | 12/2004 | Grimee et al. |
| 2007/0123508 | A1 | 5/2007 | Olsson et al. |
| 2009/0062366 | A1 | 3/2009 | Hachiya et al. |
| 2009/0203694 | A1 | 8/2009 | Hurley et al. |
| 2010/0010219 | A1 | 1/2010 | Harada et al. |
| 2011/0218199 | A1 | 9/2011 | Georges et al. |
| 2015/0173371 | A1 | 6/2015 | Mann et al. |
| 2016/0137639 | A1 | 5/2016 | Kotoku et al. |
| 2018/0077931 | A1 | 3/2018 | Stevenson et al. |
| 2018/0099935 | A1 | 4/2018 | Satterfield et al. |
| 2018/0141904 | A1 | 5/2018 | Campbell et al. |
| 2018/0213788 | A1 | 8/2018 | Satterfield et al. |
| 2020/0115337 | A1 | 4/2020 | Campbell |
| 2020/0120931 | A1 | 4/2020 | Campbell |
| 2020/0154709 | A1 | 5/2020 | McMahon |

FOREIGN PATENT DOCUMENTS

| | | |
|---|---|---|
| EP | 2336104 | 6/2011 |
| IN | 1462DEL08 | 6/2008 |
| JP | 51131870 | 11/1976 |
| JP | 52156859 | 12/1977 |
| JP | 53-056288 | 5/1978 |
| JP | 54-088114 | 7/1979 |
| JP | H0770037 | 3/1995 |
| JP | 08-269145 | 10/1996 |
| KR | 20130142477 | 12/2013 |
| RU | 2555370 | 7/2015 |
| WO | 200009481 | 2/2000 |
| WO | 2002/006512 | 1/2002 |
| WO | 2003024222 | 3/2003 |
| WO | 2004046081 | 6/2004 |
| WO | 2006081562 | 8/2006 |
| WO | 2006/127396 | 11/2006 |
| WO | 2007068376 | 6/2007 |
| WO | 2009062371 | 5/2009 |
| WO | 20120034957 | 3/2012 |
| WO | 2015084796 | 6/2015 |
| WO | 2016003997 | 1/2016 |
| WO | 2016094117 | 6/2016 |
| WO | 2016164201 | 10/2016 |
| WO | 2016176082 | 11/2016 |
| WO | 2016182780 | 11/2016 |
| WO | 2016196019 | 12/2016 |
| WO | 2016196593 | 12/2016 |
| WO | 20170023515 | 2/2017 |
| WO | 2017075559 | 5/2017 |
| WO | 2018/065311 | 4/2018 |
| WO | 20180118384 | 6/2018 |
| WO | 20180175231 | 9/2018 |
| WO | 2018222646 | 12/2018 |
| WO | 2018222647 | 12/2018 |

OTHER PUBLICATIONS

Banerjee et al., "A Stereoselective Cyclization Strategy for the Preparation of gamma-Lactams and Their Use in the Synthesis of alpha-Methyl-beta-Proline", J. Org. Chem. 2012, vol. 77, pp. 10925-10930.

Campaigne et el.; Synthesis of Some Ureidodihydrofurans and Related Pyrimidones as Potential Antimalarials; J. Med. Chem.; 1969; 339-342 (XP002278920).

Cauliez et al.; "Studies on Pyrrolidinones. On the Carbamoylation of Some Pyroglutamic Derivatives"; J. Het. Chem.; 33; 1996; 1233-1237 (XP055297107).

Hajra, S. et al., "Organocatalytic Enantioselective Conjugate Addition of Nitromethane to Alkylidinemalonates Asymmetric Synthesis of Pyrrolidine-3-Carboxylic Acid Derivatives", RSC Advances, 2013, 3, 10185-10188.

Hwang et al.; "Diastereoselective Synthesis of Oxazolidinone Derivatives and Their Antifungal Activities"; Korean J. of Med. Chem.; vol. 4, No. 1; 1994; 52-56. (XP009191451).

IPCOM000241978D; Jun. 11, 2015.

PubChem Entry CID 29937915 (4S)-4-[3-(trifluoromethyl)phenyl]pyrrolidin-2-one: May 28, 2009.

Wang et al., "Asymmetric Cyanation of Activated Olefins with Ethyl Cyanoformate Catalyzed by a Modular Titanium Catalyst", Org. Lett., 2010, vol. 12(6), pp. 1280-1283.

XP002734980; Jan. 20, 2002.
XP002734981; WO000948I; Feb. 24, 2000.
XP002759805; Jan. 20, 2002.
XP002759806; Mar. 23, 2009.

CN Decision, "Invalidation Request Examination Decision," in CN Appln. No. 201480074726.8, dated Apr. 20, 2021, 23 pages.

CN Opposition, "Request for Invalidation of a Patent Right," in CN Appln No. 201480074726.8, dated Sep. 9, 2020, 49 pages (English Translation).

CN Support, "Declaration of Aman Chandi," in CN Appln. No 201480074726.8, dated Dec. 18, 2020, 9 pages.

CN Support, "Declaration of Steven Gutteridge," in CN Appln. No. 201480074726.8, dated Dec. 18, 2020, 5 pages.

CN Support, "Declaration of Steven Gutteridge," in CN Appln. No. 201480074726.8, dated Feb. 10, 2021, 5 pages.

EP Opposition Response, "Auxiliary Request 1—marked up," in EP Appln No. 14815174.9, from response dated Jun. 25, 2021, 10 pages.

EP Opposition Response, "Auxiliary Request 1," in EP Appln No. 14815174.9, from response dated Jun. 25, 2021, 10 pages.

EP Opposition Response, "Auxiliary Request 2—marked up," in EP Appln No. 14815174.9, from response dated Jun. 25, 2021, 10 pages.

EP Opposition Response, "Auxiliary Request 2," in EP Appln No. 14815174.9, from response dated Jun. 25, 2021, 10 pages.

EP Opposition Response, "Auxiliary Request 3—marked up," in EP Appln No. 14815174.9, from response dated Jun. 25, 2021, 10 pages.

EP Opposition Response, "Auxiliary Request 3," in EP Appln No. 14815174.9, from response dated Jun. 25, 2021, 9 pages.

EP Opposition Response, "Auxiliary Request 4—marked up," in EP Appln No. 14815174.9, from response dated Jun. 25, 2021, 10 pages.

EP Opposition Response, "Auxiliary Request 4," in EP Appln No. 14815174.9, from response dated Jun. 25, 2021, 9 pages.

EP Opposition Response, "Auxiliary Request 5—marked up," in EP Appln No. 14815174.9, from response dated Jun. 25, 2021, 11 pages.

(56) References Cited

OTHER PUBLICATIONS

EP Opposition Response, "Auxiliary Request 5," in EP Appln No. 14815174.9, from response dated Jun. 25, 2021, 7 pages.
EP Opposition Response, "Data testing herbicidal activity of compounds IC1*, IC3* andIC6 against plants," Exhibit D16 in EP Appln. No. 14815174.9, from response dated Jun. 25, 2021, 5 pages.
EP Opposition Response, "Experimental data for further compounds," Exhibit D19 in EP Appln. No. 14815174.9, from response dated Jun. 25, 2021, 9 pages.
EP Opposition Response, "HRAC Mode of Action Classification 2021," Exhibit D21 in EP Appln. No. 14815174.9, from response dated Jun. 25, 2021, 2 pages.
EP Opposition Response, "Press Release—Novel herbicide tetflupyrolimet from FMC Corporation granted a new mode of action classification," Exhibit D20 in EP Appln. No 14815174.9, dated Apr. 8, 2021, 3 pages.
EP Opposition Response, "Submission In Opposition Proceedings—FMC," in EP Appln. No. 14815174.9, dated Jun. 25, 2021, 43 pages.
EP Opposition, "Cudney—Why Herbicides Are Selective," Exhibit D22 in EP Appln. No. 14815174.9, 1996 Symposium Proceedings, 3 pages.
EP Opposition, "Notice of Opposition to a European Patent," in EP Appln. No. 14815174.9, dated Aug. 31, 2020, 55 pages.
EP Opposition, "English translation of the second amendments based on granted claims in CNIPA Decision," Exhibit D28 in EP Appln. No 14815174.9, dated Apr. 15, 2021, 3 pages.
EP Opposition, "Smith—Organic Chemistry, An Acid-Base Approach," Exhibit D25 in EP Appln. No. 14815174.9, CRC Press, Taylor & Francis Group, LLC, 2011, pp. 24-32, 23 pages.
EP Opposition, "Submission In Opposition Proceedings—Syngenta," in EP Appln. No. 14815174.9, dated Nov. 5, 2020, 68 pages.
EP Opposition, "Summons to Attend Oral Proceedings Pursuant to Rule 115(1) EPC," in EP Appln. No. 14815174.9, dated Jul. 16, 2021, 14 pages.
EP Opposition, "TechLine Invasive Plant News—Factors Affecting Herbicide Performance," Exhibit D23 in EP Appln. No. 14815174.9, dated Jun. 2019, 9 pages.
EP Opposition, "US-PTAB Decision in relation to U.S. Pat. No. 10,294,202 B2," Exhibit D30 in EP Appln. No. 14815174.9, dated Aug. 31, 2021, 66 pages.
EP Opposition, "Walsh—Enzymatic Reaction Mechanisms," Exhibit D26 in EP Appln. No. 14815174.9, W. H. Freeman and Company, 1979, Chapter 2, pp. 24-48, 27 pages.
EP Opposition, "Williams—Opportunities for Chiral Agrochemicals," Exhibit D24 in EP Appln. No. 14815174.9, Pestic. Sci., 1996, 46:3-9.
EP Opposition, "Written Submission," in EP Appln. No. 14815174.9, dated Dec. 14, 2021, 3 pages.
EP Opposition, "Written Submission," in EP Appln. No. 14815174.9, dated Dec. 7, 2021, 2 pages.
EP Opposition, "Written Submission," in EP Appln. No. 14815174.9, dated Nov. 25, 2021, 32 pages.
EP Opposition, "Written Submission," in EP Appln. No. 14815174.9, dated Nov. 30, 2021, 6 pages.
IN Opposition, "Declaration of Dhaval Dayabhai Diyora," in IN Appln. No. 201617018886, dated Jun. 1, 2016, 60 pages.
V. G. Belikov, Pharmaceutical Chemistry, Chapter 2.6, "The relationship between chemical structure, properties of substances and their effect on the body", M.: MEDpress-inform, 2007, p. 27-29.
Nichols et al. "Preparation of Pyrrolidine-Based PDE4 Inhibitors via Enantioselective Conjugate Addition of alpha-substituteed Malonates to Aromatic Nitroalkenes", Organic Letters 2006, vol. 8 pp. 1495-1498.
Yan et al., "Novel chiral thioureas for highly enantioselective Michael reactions of malonates to nitroalkenes", Chinese Chemical Letters, 2009, vol. 20, pp. 310-313.
Tsubbogo, et al., "Multistep Continuous-flow synthesis of (R)- and (S)-rolipram using heterogeneous catalysts", Nature, Apr. 16, 2015, vol. 520, pp. 329-332, S1-S17.
Gavin et al., Selective Michael additions to alkylidinemalonates using thiourea-based bifunctional organocatalysts, ARKIVOC, 2013, vol. 4. pp. 76-87.
Almasi et al., "Chiral 2-Aminobenzimidazoles as Recoverable Organocatalysts for the Addition of 1,3-Dicarbonyl Compounds to Nitroalkenes", J Org Chem., 2009, vol. 74, p. 6163-6168.
Michel et al., "Synthesis and antidepressant properties of 2-amino-4-phenyl-1-pyrrolone derivatives", European Journal of Medicinal Chemistry, 1978, vol. 13, p. 75.

\* cited by examiner

PYRROLIDINONES AND A PROCESS TO PREPARE THEM

FIELD OF THE INVENTION

This invention relates to certain pyrrolidinones, intermediates, and methods to prepare them.

BACKGROUND OF THE INVENTION

WO 2015/084796 and WO 2016/196593 disclose a variety of substituted cyclic amides, a method using them as a herbicide, and methods to prepare them. WO 2016/094117 discloses certain 3-oxo-3-(arylamino)propanoates, their salts and compositions, a process to prepare them and their use in preparing certain pyrrolidinones useful as herbicides.

The pyrrolidinones and a process to prepare them of the present invention are not disclosed in these publications.

SUMMARY OF THE INVENTION

This application is directed to a compound of Formula II and salts thereof

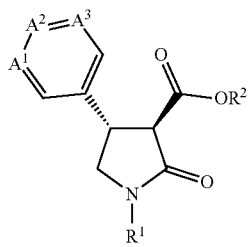

II wherein
  $A^1$ is $CCF_3$, $A^2$ is CH and $A^3$ is CH; or
  $A^1$ is CH, $A^2$ is $CCF_3$ and $A^3$ is CH; or
  $A^1$ is N, $A^2$ is $CCF_3$ and $A^3$ is CH; or
  $A^1$ is $CCH_3$, $A^2$ is N and $A^3$ is $COCHF_2$;
  $R^1$ is $C_1$-$C_4$ alkyl; and
  $R^2$ is H or $C_1$-$C_4$ alkyl.

This application is also directed to a process for preparing a compound of Formula II-A

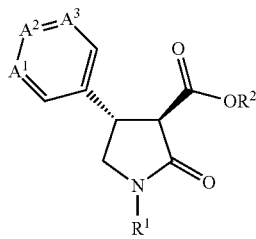

II-A wherein
  $A^1$ is $CCF_3$, $A^2$ is CH and $A^3$ is CH; or
  $A^1$ is CH, $A^2$ is $CCF_3$ and $A^3$ is CH; or
  $A^1$ is N, $A^2$ is $CCF_3$ and $A^3$ is CH; or
  $A^1$ is $CCH_3$, $A^2$ is N and $A^3$ is $COCHF_2$;
  $R^1$ is $C_1$-$C_4$ alkyl; and
  $R^2$ is H comprising alkylating a compound of Formula III

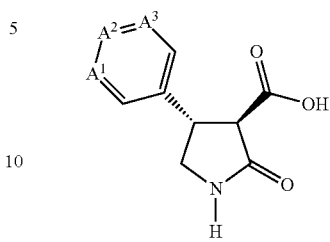

III wherein
  $A^1$ is $CCF_3$, $A^2$ is CH and $A^3$ is CH; or
  $A^1$ is CH, $A^2$ is $CCF_3$ and $A^3$ is CH; or
  $A^1$ is N, $A^2$ is $CCF_3$ and $A^3$ is CH; or
  $A^1$ is $CCH_3$, $A^2$ is N and $A^3$ is $COCHF_2$
with an alkylating agent.

This application is also directed to a compound of Formula IV and salts thereof

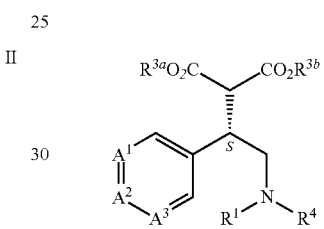

IV wherein
  $A^1$ is $CCF_3$, $A^2$ is CH and $A^3$ is CH; or
  $A^1$ is CH, $A^2$ is $CCF_3$ and $A^3$ is CH; or
  $A^1$ is N, $A^2$ is $CCF_3$ and $A^3$ is CH; or
  $A^1$ is $CCH_3$, $A^2$ is N and $A^3$ is $COCHF_2$;
  $R^1$ is $C_1$-$C_4$ alkyl;
  each $R^{3a}$ and $R^{3b}$ is independently $C_1$-$C_4$ alkyl; and
  $R^4$ is substituted or unsubstituted benzyl.

This application is also directed to a process for preparing a compound of Formula II-B

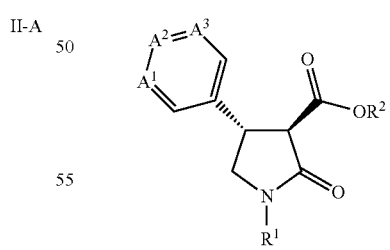

II-B wherein
  $A^1$ is $CCF_3$, $A^2$ is CH and $A^3$ is CH; or
  $A^1$ is CH, $A^2$ is $CCF_3$ and $A^3$ is CH; or
  $A^1$ is N, $A^2$ is $CCF_3$ and $A^3$ is CH; or
  $A^1$ is $CCH_3$, $A^2$ is N and $A^3$ is $COCHF_2$;
  $R^1$ is $C_1$-$C_4$ alkyl; and
  $R^2$ is $C_1$-$C_4$ alkyl comprising reducing a compound of Formula IV

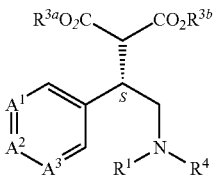

wherein
 A$^1$ is CCF$_3$, A$^2$ is CH and A$^3$ is CH; or
 A$^1$ is CH, A$^2$ is CCF$_3$ and A$^3$ is CH; or
 A$^1$ is N, A$^2$ is CCF$_3$ and A$^3$ is CH; or
 A$^1$ is CCH$_3$, A$^2$ is N and A$^3$ is COCHF$_2$;
 R$^1$ is C$_1$-C$_4$ alkyl;
 each R$^{3a}$ and R$^{3b}$ is independently C$_1$-C$_4$ alkyl; and
 R$^4$ is substituted or unsubstituted benzyl
with a reducing agent.

This application is also directed to a process for preparing a compound of Formula IV

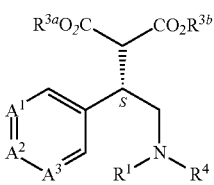

wherein
 A$^1$ is CCF$_3$, A$^2$ is CH and A$^3$ is CH; or
 A$^1$ is CH, A$^2$ is CCF$_3$ and A$^3$ is CH; or
 A$^1$ is N, A$^2$ is CCF$_3$ and A$^3$ is CH; or
 A$^1$ is CCH$_3$, A$^2$ is N and A$^3$ is COCHF$_2$;
 R$^1$ is C$_1$-C$_4$ alkyl;
 each R$^{3a}$ and R$^{3b}$ is independently C$_1$-C$_4$ alkyl; and
 R$^4$ is substituted or unsubstituted benzyl
comprising reacting a compound of Formula V or a salt thereof

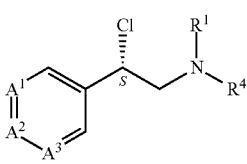

wherein
 A$^1$ is CCF$_3$, A$^2$ is CH and A$^3$ is CH; or
 A$^1$ is CH, A$^2$ is CCF$_3$ and A$^3$ is CH; or
 A$^1$ is N, A$^2$ is CCF$_3$ and A$^3$ is CH; or
 A$^1$ is CCH$_3$, A$^2$ is N and A$^3$ is COCHF$_2$;
 R$^1$ is C$_1$-C$_4$ alkyl; and
 R$^4$ is substituted or unsubstituted benzyl
with a di-(C$_1$-C$_4$ alkyl) malonate.

This application is also directed to a process for preparing a compound of Formula I

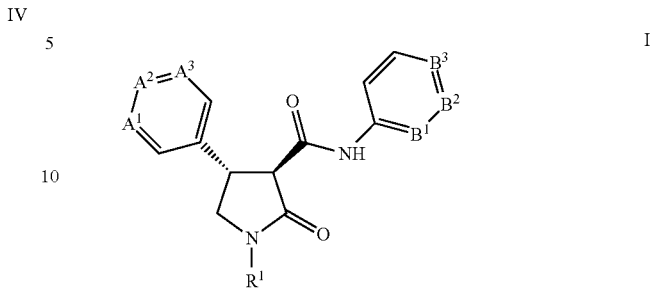

wherein
 A$^1$ is CCF$_3$, A$^2$ is CH and A$^3$ is CH; or
 A$^1$ is CH, A$^2$ is CCF$_3$ and A$^3$ is CH; or
 A$^1$ is N, A$^2$ is CCF$_3$ and A$^3$ is CH; or
 A$^1$ is CCH$_3$, A$^2$ is N and A$^3$ is COCHF$_2$;
 R$^1$ is C$_1$-C$_4$ alkyl;
 B$^1$ is CF, B$^2$ is CH and B$^3$ is CH; or
 B$^1$ is CF, B$^2$ is CF and B$^3$ is CH; or
 B$^1$ is CF, B$^2$ is N and B$^3$ is CF
comprising contacting a compound of Formula II-A

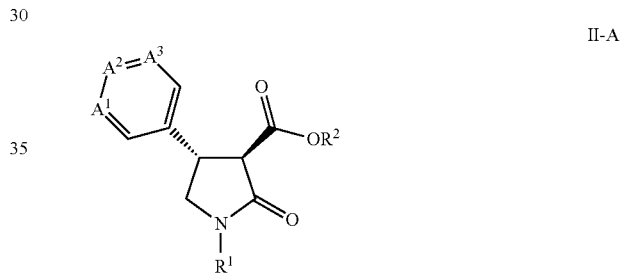

prepared by the process as described in the Summary of the Invention for preparing a compound of Formula II-A
wherein
 A$^1$ is CCF$_3$, A$^2$ is CH and A$^3$ is CH; or
 A$^1$ is CH, A$^2$ is CCF$_3$ and A$^3$ is CH; or
 A$^1$ is N, A$^2$ is CCF$_3$ and A$^3$ is CH; or
 A$^1$ is CCH$_3$, A$^2$ is N and A$^3$ is COCHF$_2$;
 R$^1$ is C$_1$-C$_4$ alkyl; and
 R$^2$ is H
with a compound of Formula VI

wherein
 B$^1$ is CF, B$^2$ is CH and B$^3$ is CH; or
 B$^1$ is CF, B$^2$ is CF and B$^3$ is CH; or
 B$^1$ is CF, B$^2$ is N and B$^3$ is CF.

This application is also directed to a process for preparing a compound of Formula I

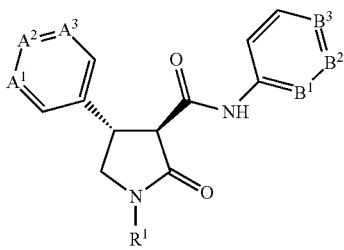

I wherein
$A^1$ is $CCF_3$, $A^2$ is CH and $A^3$ is CH; or
$A^1$ is CH, $A^2$ is $CCF_3$ and $A^3$ is CH; or
$A^1$ is N, $A^2$ is $CCF_3$ and $A^3$ is CH; or
$A^1$ is $CCH_3$, $A^2$ is N and $A^3$ is $COCHF_2$;
$R^1$ is $C_1$-$C_4$ alkyl;
$B^1$ is CF, $B^2$ is CH and $B^3$ is CH; or
$B^1$ is CF, $B^2$ is CF and $B^3$ is CH; or
$B^1$ is CF, $B^2$ is N and $B^3$ is CF
comprising contacting a compound of Formula II-B

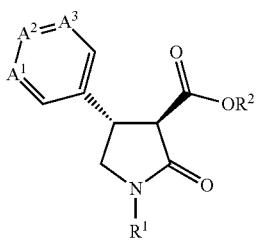

II-B prepared by the process as described in the Summary of the Invention for preparing a compound of Formula II-B wherein
$A^1$ is $CCF_3$, $A^2$ is CH and $A^3$ is CH; or
$A^1$ is CH, $A^2$ is $CCF_3$ and $A^3$ is CH; or
$A^1$ is N, $A^2$ is $CCF_3$ and $A^3$ is CH; or
$A^1$ is $CCH_3$, $A^2$ is N and $A^3$ is $COCHF_2$;
$R^1$ is $C_1$-$C_4$ alkyl; and
$R^2$ is $C_1$-$C_4$ alkyl
with a compound of Formula VI

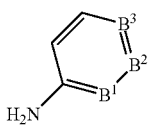

VI wherein
$B^1$ is CF, $B^2$ is CH and $B^3$ is CH; or
$B^1$ is CF, $B^2$ is CF and $B^3$ is CH; or
$B^1$ is CF, $B^2$ is N and $B^3$ is CF.

DETAILS OF THE INVENTION

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process, method, article, or apparatus that comprises a list of elements is not necessarily limited to only those elements but may include other elements not expressly listed or inherent to such composition, mixture, process, method, article, or apparatus.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition, method or apparatus that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising," it should be readily understood that (unless otherwise stated) the description should be interpreted to also describe such an invention using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

In the above recitations, the term "alkyl" includes straight-chain or branched alkyl, such as, methyl, ethyl, n-propyl, i-propyl, or the different butyl isomers.

"Unsubstituted benzyl" refers to a benzyl group without any substitution (i.e. —$CH_2Ph$). "Substituted benzyl" refers to a benzyl group substituted on either the methylene moiety or the phenyl moiety that make up the benzyl group. Substitution of the benzyl group is by $C_1$-$C_4$ alkyl, $C_1$-$C_4$ alkoxy or $C_2$-$C_4$ alkenyl where the term "alkyl" is defined above, "alkoxy" includes, for example, methoxy, ethoxy, n-propyloxy, isopropyloxy and the different butoxy isomers, and "alkenyl" includes straight-chain or branched alkenes such as ethenyl, 1-propenyl, 2-propenyl, and the different butenyl isomers. "Alkenyl" also includes polyenes such as 1,2-propadienyl.

The total number of carbon atoms in a substituent group is indicated by the "$C_i$-$C_j$" prefix where i and j are numbers from 1 to 4. For example, $C_1$-$C_4$ alkyl designates methyl through butyl; $C_2$ alkoxy designates $CH_3CH_2O$—; $C_3$ alkenyl designates, for example, $CH_2$=$CHCH_2$—.

In the compounds of Formulae I, II, II-A, II-B, III, IV and V the ring containing variables $A^1$, $A^2$ and $A^3$ can be represented by the following structures shown in Exhibit 1 where the bond projecting to the right indicates the attachment point to the remainder of Formula I, II, II-A, II-B, III, IV or V.

Exhibit 1

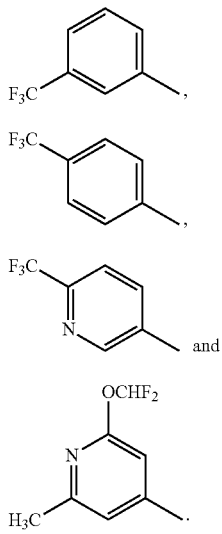

In the compounds of Formulae I and VI the ring containing variables $B^1$, $B^2$ and $B^3$ can be represented by the following structures shown in Exhibit 2 where the bond projecting to the left indicates the attachment point to the remainder of Formula I or the —NH$_2$ of Formula VI.

Exhibit 2

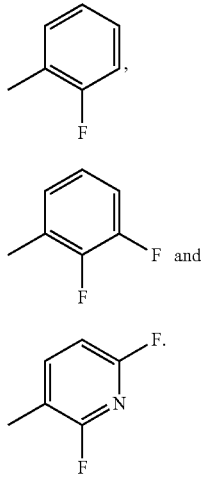

The compounds of this invention (i.e. the compounds of Formulae I and VI) can exist as one or more stereoisomers. The various stereoisomers include enantiomers, diastereomers, atropisomers and geometric isomers. Stereoisomers are isomers of identical constitution but differing in the arrangement of their atoms in space and include enantiomers, diastereomers, cis-trans isomers (also known as geometric isomers) and atropisomers. Atropisomers result from restricted rotation about single bonds where the rotational barrier is high enough to permit isolation of the isomeric species. The methods of this invention may yield compounds containing mixtures of enantiomers, diastereomers, atropisomers and geometric isomers. One skilled in the art will know how to separate, enrich, and/or to selectively prepare said stereoisomers. The compounds of the invention (or the process used to prepare them) may be present (or may be prepared) as a mixture of stereoisomers, individual stereoisomers or as an optically active form.

For example the C═O(NH) moiety (bonded to the carbon at the 3-position of the pyrrolidinone ring) and the ring containing variables $A^1$, $A^2$ and $A^3$ (bonded to the carbon at the 4-position of the pyrrolidinone ring) are generally found in the trans configuration. Each of these two carbon atoms posses a chiral center. The two most prevelant pairs of enantiomers are depicted as Formula I' and Formula I" where the chiral centers are identified (i.e. as 3S,4S or as 3R,4R). While this invention pertains to all stereoisomers, the preferred enantiomeric pair for biological operability is identified as Formula I' (i.e. the 3S,4S configuration), and preferably the trans configuration. For a comprehensive discussion of all aspects of stereoisomerism, see Ernest L. Eliel and Samuel H. Wilen, *Stereochemistry of Organic Compounds*, John Wiley & Sons, 1994.

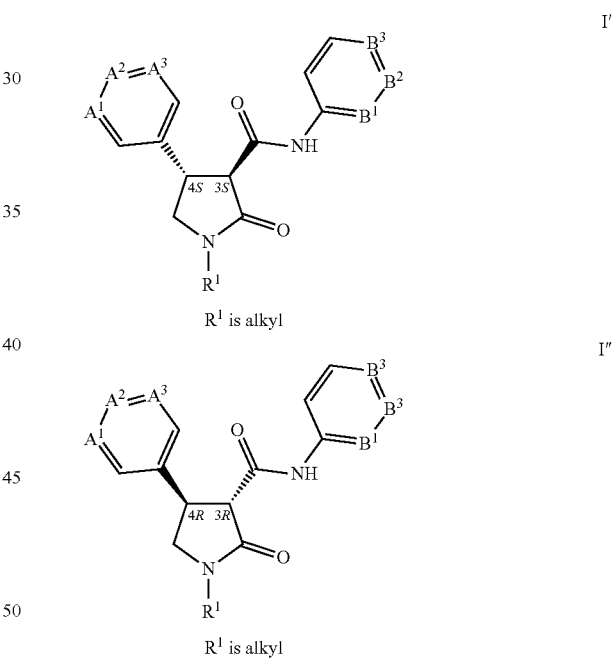

Molecular depictions drawn herein follow standard conventions for depicting stereochemistry. To indicate stereoconfiguration, bonds rising from the plane of the drawing and towards the viewer are denoted by solid wedges wherein the broad end of the wedge is attached to the atom rising from the plane of the drawing towards the viewer. Bonds going below the plane of the drawing and away from the viewer are denoted by dashed wedges wherein the narrow end of the wedge is attached to the atom closer to the viewer. Constant width lines indicate bonds with a direction opposite or neutral relative to bonds shown with solid or dashed wedges; constant width lines also depict bonds in molecules or parts of molecules in which no particular stereoconfiguration is intended to be specified.

This invention comprises racemic mixtures, for example, equal amounts of the enantiomers of Formulae I' and I" as well as the corresponding pyrrolidinones of Formulae II, II-A, II-B and III. Likewise, the invention includes racemic mixtures of pyrrolidinone compounds of Formulae IV and V. In addition, this invention includes compounds that are enriched compared to the racemic mixture. Also included are the essentially pure enantiomers of compounds of Formulae I, II, II-A, II-B, III, IV and V.

When enantiomerically enriched, one enantiomer is present in greater amounts than the other, and the extent of enrichment can be defined by an expression of enantiomeric ratio (ER) expressed as the relative area % of the two entantiomer determined by chiral high-performance liquid chromatography.

Preferably the compounds prepared by the present processes of this invention have at least a 50% ER; more preferably at least a 75% ER; still more preferably at least a 90% ER; and the most preferably at least a 94% ER of the more active isomer. Of particular note are enantiomerically pure embodiments of the more desired isomer. The enantiomeric excess (e.e.) can be calculated from the enantiomeric ratio.

Compounds of Formulae II and IV typically exist in more than one form, and thus include all crystalline and non-crystalline forms of the compounds they represent. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due the presence or absence of co-crystallized water or other molecules, which can be weakly or strongly bound in the lattice. Polymorphs can differ in such chemical and physical properties as crystal shape, density, hardness, color, chemical stability, melting point, hygroscopicity, suspensibility and dissolution rate. One skilled in the art will appreciate that a polymorph of the compounds of Formulae II or IV can exhibit beneficial effects (e.g., suitability for isolation, or used in subsequent steps to improve yield) relative to another polymorph or a mixture of polymorphs of the same compounds of Formulae II or IV. Preparation and isolation of a particular polymorph of the compounds of Formulae II or IV can be achieved by methods known to those skilled in the art including, for example, crystallization using selected solvents and temperatures. The methods of preparing the compounds of Formulae I, II, II-A, II-B, III, IV and V may produce one or more specific polymorph(s). For a comprehensive discussion of polymorphism see R. Hilfiker, Ed., *Polymorphism in the Pharmaceutical Industry*, Wiley-VCH, Weinheim, 2006.

One skilled in the art will appreciate that not all nitrogen-containing heterocycles can form N-oxides since the nitrogen requires an available lone pair for oxidation to the oxide; one skilled in the art will recognize those nitrogen-containing heterocycles which can form N-oxides. One skilled in the art will also recognize that tertiary amines can form N-oxides.

Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

The salts of compounds of Formulae II and IV include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When compounds of Formulae II and IV contain an acidic moiety such as a carboxylic acid or phenol, salts also include those formed with organic or inorganic bases such as pyridine, triethylamine or ammonia, or amides, hydrides, hydroxides or carbonates of sodium, potassium, lithium, calcium, magnesium or barium. Accordingly, the present invention comprises compounds selected from compounds of Formulae II and IV, N-oxides and agriculturally suitable salts thereof.

Embodiments of the present invention as described in the Summary of the Invention include:

Embodiment A1. A compound of Formula II and salts thereof as described in the Summary of the Invention wherein $A^1$ is $CCF_3$, $A^2$ is CH and $A^3$ is CH.

Embodiment A2. A compound of Formula II and salts thereof as described in the Summary of the Invention wherein $A^1$ is CH, $A^2$ is $CCF_3$ and $A^3$ is CH.

Embodiment A3. A compound of Formula II and salts thereof as described in the Summary of the Invention wherein $A^1$ is N, $A^2$ is $CCF_3$ and $A^3$ is CH; or $A^1$ is $CCH_3$, $A^2$ is N and $A^3$ is $COCHF_2$.

Embodiment A4. A compound of any one of Embodiments $A^1$ through $A^3$ wherein $R^2$ is H.

Embodiment A5. A compound of any one of Embodiments $A^1$ through $A^3$ wherein $R^2$ is $C_1$-$C_4$ alkyl.

Embodiment A6. A compound of Embodiment A5 wherein $R^2$ is methyl, ethyl, n-propyl, i-propyl, n-butyl or t-butyl.

Embodiment A7. A compound of Embodiment A6 wherein $R^2$ is methyl or ethyl.

Embodiment A8. A compound of Embodiment A7 wherein $R^2$ is methyl.

Embodiment A9. A compound of any one of Embodiments $A^1$ through $A^3$ or $A^5$ through $A^8$ wherein $R^2$ is other than H.

Embodiment A10. A compound of any one of Embodiments $A^1$ through $A^9$ wherein $R^1$ is methyl, ethyl or propyl.

Embodiment A11. A compound of Embodiment A10 wherein $R^1$ is methyl or ethyl.

Embodiment A12. A compound of Embodiment A11 wherein $R^1$ is methyl.

Embodiment A13. A compound of Formula II selected from the group consisting of methyl (3R,4S)-1-methyl- 2-oxo-4-[3-(trifluoromethyl)phenyl]-3-pyrrolidinecarboxylate; and (3R,4S)-1-methyl-2-oxo-4-[3-(trifluoromethyl)phenyl]-3-pyrrolidinecarboxylic acid.

Embodiment A14. A compound of Embodiment A13 that is methyl (3R,4S)-1-methyl-2-oxo-4-[3-(trifluoromethyl)phenyl]-3-pyrrolidinecarboxylate.

Embodiment A15. A compound of Embodiment A13 that is (3R,4S)-1-methyl-2-oxo-4-[3-(trifluoromethyl)phenyl]-3-pyrrolidinecarboxylic acid.

Embodiment B1. The process as described in the Summary of the Invention for preparing a compound of Formula II-A wherein $A^1$ is $CCF_3$, $A^2$ is CH and $A^3$ is CH.

Embodiment B2. The process as described in the Summary of the Invention for preparing a compound of Formula II-A wherein A is CH, $A^2$ is $CCF_3$ and $A^3$ is CH.

Embodiment B3. The process as described in the Summary of the Invention for preparing a compound of Formula II-A wherein $A^1$ is N, $A^2$ is $CCF_3$ and $A^3$ is CH; or $A^1$ is $CCH_3$, $A^2$ is N and $A^3$ is $COCHF_2$.

Embodiment B4. The process of any one of Embodiments B1 through B3 wherein $R^1$ is methyl, ethyl or propyl.

Embodiment B5. The process of Embodiment B4 wherein $R^1$ is methyl or ethyl.

Embodiment B6. The process of Embodiment B5 wherein $R^1$ is methyl.

Embodiment B7. The process of any one of Embodiments B1 through B6 wherein in a compound of Formula III, $A^1$ is $CCF_3$, $A^2$ is CH and $A^3$ is CH.

Embodiment B8. The process of any one of Embodiments B1 through B6 wherein in a compound of Formula III, $A^1$ is CH, $A^2$ is $CCF_3$ and $A^3$ is CH.

Embodiment B9. The process of any one of Embodiments B1 through B6 wherein in a compound of Formula III, $A^1$ is N, $A^2$ is $CCF_3$ and $A^3$ is CH; or $A^1$ is $CCH_3$, $A^2$ is N and $A^3$ is $COCHF_2$.

Embodiment B10. The process of any one of Embodiments B1 through B9 wherein the alkylating agent comprises a dialkylsulfate.

Embodiment B11. The process of Embodiment B10 wherein the alkylating agent is selected from the group consisting of dimethylsulfate, diethylsulfate or dipropylsulfate.

Embodiment B12. The process of Embodiment B11 wherein the alkylating agent is selected from the group consisting of dimethylsulfate or diethylsulfate.

Embodiment B13. The process of Embodiment B12 wherein the alkylating agent is dimethylsulfate.

Embodiment B14. The process of any one of Embodiments B1 through B13 wherein the alkylating is performed in a suitable solvent.

Embodiment B15. The process of Embodiment B14 wherein the suitable solvent is an alcohol.

Embodiment B16. The process of Embodiment B15 wherein the suitable solvent is selected from the group consisting of methanol, ethanol, isopropanol and t-butanol.

Embodiment B17. The process of Embodiment B14 wherein the suitable solvent is acetonitrile.

Embodiment B18. The process of Embodiment B14 wherein the suitable solvent is a mixture of water and acetonitrile.

Embodiment B19. The process of any one of Embodiments B1 through B9 wherein the alkylating agent comprises bromomethane and is performed in the presence of potassium t-butoxide and is preformed in tetrahydrofuran.

Embodiment B20. The process of any one of Embodiments B1 through B9 wherein the alkylating is performed in the presence of a base.

Embodiment B21. The process of Embodiment B20 wherein the base is an inorganic base.

Embodiment B22. The process of Embodiment B21 wherein the base is potassium hydroxide.

Embodiment C1. A compound of Formula IV and salts thereof as described in the Summary of the Invention wherein $A^1$ is $CCF_3$, $A^2$ is CH and $A^3$ is CH.

Embodiment C2. A compound of Formula IV and salts thereof as described in the Summary of the Invention wherein $A^1$ is CH, $A^2$ is $CCF_3$ and $A^3$ is CH.

Embodiment C3. A compound of Formula IV and salts thereof as described in the Summary of the Invention wherein A is N, $A^2$ is $CCF_3$ and $A^3$ is CH; or A is $CCH_3$, $A^2$ is N and $A^3$ is $COCHF_2$.

Embodiment C4. A compound of any one of Embodiments C1 through C3 wherein $R^1$ is methyl, ethyl or propyl.

Embodiment C5. A compound of Embodiment C4 wherein $R^1$ is methyl or ethyl.

Embodiment C6. A compound of Embodiment C5 wherein $R^1$ is methyl.

Embodiment C7. A compound of any one of Embodiments C1 through C6 wherein each $R^{3a}$ and $R^{3b}$ is independently methyl, ethyl or propyl.

Embodiment C8. A compound of Embodiment C7 wherein each $R^{3a}$ and $R^{3b}$ is independently methyl or ethyl.

Embodiment C9. A compound of Embodiment C8 wherein each $R^{3a}$ and $R^{3b}$ is independently methyl.

Embodiment C10. A compound of any one of Embodiments C1 through C9 wherein $R^4$ is substituted benzyl.

Embodiment C11. A compound of Embodiment C10 wherein $R^4$ is benzyl substituted with $C_1$-$C_4$ alkyl, $C_1$-$C_4$ alkoxy or C2-$C_4$ alkenyl.

Embodiment C12. A compound of Embodiment C10 wherein $R^4$ is unsubstituted benzyl.

Embodiment C13. A compound of Formula IV that is 1,3-dimethyl 2-[(1S)-2-[methyl(phenylmethyl)amino]-1-[3-(trifluoromethyl)phenyl]ethyl]propanedioate.

Embodiment D1. The process as described in the Summary of the Invention for preparing a compound of Formula II-B wherein $A^1$ is $CCF_3$, $A^2$ is CH and $A^3$ is CH.

Embodiment D2. The process as described in the Summary of the Invention for preparing a compound of Formula II-B wherein $A^1$ is CH, $A^2$ is $CCF_3$ and $A^3$ is CH.

Embodiment D3. The process as described in the Summary of the Invention for preparing a compound of Formula II-B wherein $A^1$ is N, $A^2$ is $CCF_3$ and $A^3$ is CH; or $A^1$ is $CCH_3$, $A^2$ is N and $A^3$ is $COCHF_2$.

Embodiment D4. The process of any one of Embodiments D1 through D3 wherein $R^2$ is $C_1$-$C_4$ alkyl.

Embodiment D5. The process of Embodiment D4 wherein $R^2$ is methyl, ethyl, n-propyl, i-propyl, n-butyl or t-butyl.

Embodiment D6. The process of Embodiment D5 wherein $R^2$ is methyl or ethyl.

Embodiment D7. The process of Embodiment D6 wherein $R^2$ is methyl.

Embodiment D8. The process of any one of Embodiments D1 through D7 wherein $R^1$ is methyl, ethyl or propyl.

Embodiment D9. The process of Embodiment D8 wherein $R^1$ is methyl or ethyl.

Embodiment D10. The process of Embodiment D9 wherein $R^1$ is methyl.

Embodiment D11. The process of any one of Embodiments D1 through D10 wherein in a compound of Formula IV, $A^1$ is $CCF_3$, $A^2$ is CH and $A^3$ is CH.

Embodiment D12. The process of any one of Embodiments D1 through D10 wherein in a compound of Formula IV, $A^1$ is CH, $A^2$ is $CCF_3$ and $A^3$ is CH.

Embodiment D13. The process of any one of Embodiments D1 through D10 wherein in a compound of Formula IV, $A^1$ is N, $A^2$ is $CCF_3$ and $A^3$ is CH; or $A^1$ is $CCH_3$, $A^2$ is N and $A^3$ is $COCHF_2$.

Embodiment D14. The process of any one of Embodiments D1 through D13 wherein in a compound of Formula IV, $R^1$ is methyl, ethyl or propyl.

Embodiment D15. The process of Embodiment D14 wherein in a compound of Formula IV, $R^1$ is methyl or ethyl.

Embodiment D16. The process of Embodiment D15 wherein in a compound of Formula IV, $R^1$ is methyl.

Embodiment D17. The process of any one of Embodiments D1 through D16 wherein in a compound of Formula IV, each $R^{3a}$ and R3h is independently methyl, ethyl or propyl.

Embodiment D18. The process of Embodiment D17 wherein in a compound of Formula IV, each $R^{3a}$ and $R^{3b}$ is independently methyl or ethyl.

Embodiment D19. The process of Embodiment D18 wherein in a compound of Formula IV, each $R^{3a}$ and $R^{3b}$ is independently methyl.

Embodiment D20. The process of any one of Embodiments D1 through D19 wherein in a compound of Formula IV, $R^4$ is unsubstituted benzyl.

Embodiment D21. The process of any one of Embodiments D1 through D19 wherein in a compound of Formula IV, $R^4$ is substituted benzyl.

Embodiment D22. The process of Embodiment D21 wherein $R^4$ is benzyl substituted with $C_1$-$C_4$ alkyl, $C_1$-$C_4$ alkoxy or $C_2$-$C_4$ alkenyl.

Embodiment D23. The process of any one of Embodiments D1 through D22 wherein the reducing is performed in the presence of a reducing agent.

Embodiment D24. The process of Embodiment D23 wherein the reducing agent comprises catalyst.

Embodiment D25. The process of Embodiment D24 wherein the reducing agent is selected from the group consisting of platinum(I), palladium(II) and nickel(I).

Embodiment D26. The process of Embodiment D25 wherein the reducing agent is selected from the group consisting of platinum(I) and palladium(II).

Embodiment D27. The process of Embodiment D26 wherein the reducing agent is selected from the group consisting of palladium(I) on carbon and palladium(II) hydroxide on carbon.

Embodiment D28. The process of any one of Embodiments D1 through D27 wherein the reducing is performed in a suitable solvent.

Embodiment D29. The process of Embodiment D28 wherein the suitable solvent is selected from the group consisting of methanol, ethanol, propanol, acetic acid and toluene.

Embodiment D30. The process of Embodiment D29 wherein the suitable solvent is selected from the group consisting of methanol, ethanol or propanol.

Embodiment D31. The process of Embodiment D29 wherein the suitable solvent is acetic acid.

Embodiment D32. The process of Embodiment D24 wherein the reducing agent is selected from the group consisting of platinum, palladium and nickel.

Embodiment D33. The process of Embodiment D25 wherein the reducing agent is selected from the group consisting of platinum and palladium.

Embodiment D34. The process of Embodiment D26 wherein the reducing agent is selected from the group consisting of palladium on carbon and palladium (II) hydroxide on carbon.

Embodiment E1. The process as described in the Summary of the Invention for preparing a compound of Formula IV wherein $A^1$ is $CCF_3$, $A^2$ is CH and $A^3$ is CH.

Embodiment E2. The process as described in the Summary of the Invention for preparing a compound of Formula IV wherein $A^1$ is CH, $A^2$ is $CCF_3$ and $A^3$ is CH.

Embodiment E3. The process as described in the Summary of the Invention for preparing a compound of Formula IV wherein $A^1$ is N, $A^2$ is $CCF_3$ and $A^3$ is CH; or $A^1$ is $CCH_3$, $A^2$ is N and $A^3$ is $COCHF_2$.

Embodiment E4. The process of any one of Embodiments E1 through E3 wherein $R^1$ is methyl, ethyl or propyl.

Embodiment E5. The process of Embodiment E4 wherein $R^1$ is methyl or ethyl.

Embodiment E6. The process of Embodiment E5 wherein $R^1$ is methyl.

Embodiment E7. The process of any one of Embodiments E1 through E6 wherein each $R^{3a}$ and $R^{3b}$ is independently methyl, ethyl or propyl.

Embodiment E8. The process of Embodiment E7 wherein each $R^{3a}$ and $R^{3b}$ is independently methyl or ethyl.

Embodiment E9. The process of Embodiment E8 wherein each $R^{3a}$ and $R^{3b}$ is independently methyl.

Embodiment E10. The process of any one of Embodiments E1 through E9 wherein $R^4$ is substituted benzyl or unsubstituted benzyl.

Embodiment E11. The process of Embodiment E10 wherein $R^4$ is unsubstituted benzyl.

Embodiment E12. The process of any one of Embodiments E1 through E11 wherein in a compound of Formula V or a salt thereof, $A^1$ is $CCF_3$, $A^2$ is CH and $A^3$ is CH.

Embodiment E13. The process of any one of Embodiments E1 through E11 wherein in a compound of Formula V or a salt thereof, $A^1$ is CH, $A^2$ is $CCF_3$ and $A^3$ is CH.

Embodiment E14. The process of any one of Embodiments E1 through E11 wherein in a compound of Formula V or a salt thereof, $A^1$ is N, $A^2$ is $CCF_3$ and $A^3$ is CH; or $A^1$ is $CCH_3$, $A^2$ is N and $A^3$ is $COCHF_2$.

Embodiment E15. The process of any one of Embodiments E1 through E14 wherein in a compound of Formula V or a salt thereof, $R_1$ is methyl, ethyl or propyl.

Embodiment E16. The process of Embodiment E15 wherein in a compound of Formula V or a salt thereof, $R^1$ is methyl or ethyl.

Embodiment E17. The process of Embodiment E16 wherein in a compound of Formula V or a salt thereof, $R^1$ is methyl.

Embodiment E18. The process of any one of Embodiments E12 through E17 wherein in the compound of Formula V is the hydrochloride salt.

Embodiment E19. The process of any one of Embodiments E1 through E18 wherein the di-($C_1$-$C_4$ alkyl) malonate or a salt thereof is selected from the group consisting of dimethyl malonate, diethyl malonate, diisopropyl malonate or di-n-propyl malonate or a sodium, lithium or potassium salt thereof.

Embodiment E20. The process of Embodiment E19 wherein the di-($C_1$-$C_4$ alkyl) malonate or a salt thereof is selected from the group consisting of dimethyl malonate or diethyl malonate or a sodium or potassium salt thereof.

Embodiment E21. The process of any one of Embodiments E1 through E20 wherein the reacting is performed in the presence of a suitable base.

Embodiment E22. The process of Embodiment E21 wherein the base is an inorganic base.

Embodiment E23. The process of Embodiment E22 wherein the base is selected from the group consisting of sodium methoxide, sodium ethoxide and potassium carbonate.

Embodiment E24. The process of any one of Embodiments E1 through E23 wherein the reacting is performed in the presence of a suitable solvent.

Embodiment E25. The process of Embodiment E24 wherein the solvent is an organic solvent.

Embodiment E26. The process of Embodiment E25 wherein the solvent is selected from the group consisting of acetonitrile, dichloromethane and toluene.

Embodiment E27. The process of Embodiment E26 wherein the solvent is acetonitrile.

Embodiment F1. The process as described in the Summary of the Invention for preparing a compound of Formula I wherein $A^1$ is $CCF_3$, $A^2$ is CH and $A^3$ is CH.

Embodiment F2. The process as described in the Summary of the Invention for preparing a compound of Formula I wherein $A^1$ is CH, $A^2$ is $CCF_3$ and $A^3$ is CH.

Embodiment F3. The process as described in the Summary of the Invention for preparing a compound of Formula I wherein $A^1$ is N, $A^2$ is $CCF_3$ and $A^3$ is CH; or $A^1$ is $CCH_3$, $A^2$ is N and $A^3$ is $COCHF_2$.

Embodiment F4. The process of any one of Embodiments F1 through F3 wherein B1 is CF, $B^2$ is CH and $B^3$ is CH.

Embodiment F5. The process of any one of Embodiments F1 through F3 wherein $B^1$ is CF, $B^2$ is CF and $B^3$ is CH.

Embodiment F6. The process of any one of Embodiments F1 through F3 wherein B1 is CF, $B^2$ is N and $B^3$ is CF.

Embodiment F7. The process of any one of Embodiments F1 through F6 wherein $R^1$ is methyl, ethyl or propyl.

Embodiment F8. The process of Embodiment F7 wherein $R^1$ is methyl or ethyl.

Embodiment F9. The process of Embodiment F8 wherein $R^1$ is methyl.

Embodiment F10. The process of any one of Embodiments F1 through F9 wherein in a compound of Formula II-A, At is $CCF_3$, $A^2$ is CH and $A^3$ is CH.

Embodiment F11. The process of any one of Embodiments F1 through F9 wherein in a compound of Formula II-A, $A^1$ is CH, $A^2$ is $CCF_3$ and $A^3$ is CH.

Embodiment F12. The process of any one of Embodiments F1 through F9 wherein in a compound of Formula II-A, $A^1$ is N, $A^2$ is $CCF_3$ and $A^3$ is CH; or $A^1$ is $CCH_3$, $A^2$ is N and $A^3$ is $COCHF_2$.

Embodiment F13. The process of any one of Embodiments F10 through F12 wherein R is methyl, ethyl or propyl.

Embodiment F14. The process of Embodiment F13 wherein $R^1$ is methyl or ethyl.

Embodiment F15. The process of Embodiment F14 wherein $R^1$ is methyl.

Embodiment F16. The process of any one of Embodiments F1 through F15 further comprising contacting a compound of Formula II-A with an activating agent to prepare an activated intermediate.

Embodiment F17. The process of Embodiment F16 wherein the activating agent is a halogenating agent or a sulfonating agent.

Embodiment F18. The process of any one of Embodiments F1 through F17 further comprising contacting the activated intermediate with a compound of Formula VI.

Embodiment F19. The process of Embodiment F18 wherein in a compound of Formula VI, $B^1$ is CF, $B^2$ is CH and $B^3$ is CH.

Embodiment F20. The process of Embodiment F18 wherein in a compound of Formula VI, $B^1$ is CF, $B^2$ is CF and $B^3$ is CH.

Embodiment F21. The process of Embodiment F18 wherein in a compound of Formula VI $B^1$ is CF, $B^2$ is N and $B^3$ is CF.

Embodiment F22. The process of any one of Embodiments F1 through F18 wherein the compound of Formula II-A is prepared by hydrolyzing the compound of Formula II-B.

Embodiment G1. The process as described in the Summary of the Invention for preparing a compound of Formula I wherein $A^1$ is $CCF_3$, $A^2$ is CH and $A^3$ is CH.

Embodiment G2. The process as described in the Summary of the Invention for preparing a compound of Formula I wherein $A^1$ is CH, $A^2$ is $CCF_3$ and $A^3$ is CH.

Embodiment G3. The process as described in the Summary of the Invention for preparing a compound of Formula I wherein A is N, $A^2$ is $CCF_3$ and $A^3$ is CH; or $A^1$ is $CCH_3$, $A^2$ is N and $A^3$ is $COCHF_2$.

Embodiment G4. The process of any one of Embodiments G1 through G3 wherein $R^1$ is methyl, ethyl or propyl.

Embodiment G5. The process of Embodiment G4 wherein $R^1$ is methyl or ethyl.

Embodiment G6. The process of Embodiment G5 wherein $R^1$ is methyl.

Embodiment G7. The process of any one of Embodiments G1 through G6 wherein $B^1$ is CF, $B^2$ is CH and $B^3$ is CH.

Embodiment G8. The process of any one of Embodiments G1 through G6 wherein $B^1$ is CF, $B^2$ is CF and $B^3$ is CH.

Embodiment G9. The process of any one of Embodiments G1 through G6 wherein B1 is CF, $B^2$ is N and $B^3$ is CF.

Embodiment G10. The process as described in the Summary of the Invention or any one of Embodiments G1 through G9 wherein in a compound of Formula II-B, $A^1$ is $CCF_3$, $A^2$ is CH and $A^3$ is CH.

Embodiment G11. The process as described in the Summary of the Invention or any one of Embodiments G1 through G9 wherein in a compound of Formula II-B, $A^1$ is CH, $A^2$ is $CCF_3$ and $A^3$ is CH.

Embodiment G12. The process as described in the Summary of the Invention or any one of Embodiments G1 through G9 wherein in a compound of Formula II-B, $A^1$ is N, $A^2$ is $CCF_3$ and $A^3$ is CH; or $A^1$ is $CCH_3$, $A^2$ is N and $A^3$ is $COCHF_2$.

Embodiment G13. The process of any one of Embodiments G10 through G12 wherein $R^1$ is methyl, ethyl or propyl.

Embodiment G14. The process of Embodiment G13 wherein $R^1$ is methyl or ethyl.

Embodiment G15. The process of Embodiment G14 wherein $R^1$ is methyl.

Embodiment G16. The process of any one of Embodiments G10 through G15 wherein $R^2$ is methyl, ethyl, n-propyl, i-propyl, n-butyl or t-butyl.

Embodiment G17. The process of Embodiment G16 wherein $R^2$ is methyl or ethyl.

Embodiment G18. The process of Embodiment G17 wherein $R^2$ is methyl.

Embodiment G19. The process of any one of Embodiments G1 through G18 wherein in a compound of Formula VI, $B^1$ is CF and $B^2$ is CH.

Embodiment G20. The process of any one of Embodiments G1 through G18 wherein in a compound of Formula VI, B is CF and $B^2$ is CF.

Embodiment G21. The process of the Summary of the Invention or any one of Embodiments G1 through G20 wherein the contacting is performed above ambient temperature.

Embodiment G22. The process of Embodiment G21 wherein the contacting is performed above 100° C.

Embodiment G23. The process of Embodiment G21 wherein the contacting is performed above 120° C.

Embodiment G24. The process of Embodiment G21 wherein the contacting is performed above 140° C.

Embodiment G25. The process of Embodiment G21 wherein the contacting is performed above 160° C.

Embodiment G26. The process of any one of Embodiments G21 through G25 wherein the contacting is performed below 200° C.

Embodiment G27. The process of any one of Embodiments G1 through G21 wherein the contacting is performed at the boiling point of a compound of Formula VI.

Embodiment G28. The process of any one of Embodiments G1 through G27 wherein the contacting is performed in a suitable solvent.

Embodiment G29. The process of Embodiment G28 wherein the solvent comprises a compound of Formula VI.

Embodiment G30. The process of Embodiment G28 wherein the suitable solvent is selected from toluene, xylenes or chlorobenzene.

Embodiment G31. The process of Embodiment G30 wherein the suitable solvent is xylenes.

Embodiment H. The process for preparing a compound of Formula I as described in the Summary of the Invention or any one of Embodiments F1 through F22 wherein a compound of Formula II-A is prepared using the method described in the Summary of the Invention or any one of Embodiments B1 through B16 comprising alkylating a compound of Formula III.

Embodiment H2. The process for preparing a compound of Formula I as described in the Summary of the Invention or any one of Embodiments F1 through F22 wherein a compound of Formula II-A is prepared by first hydrolyzing the compound of Formula II-B.

Embodiment H3. The process for preparing a compound of Formula I as described in the Summary of the Invention or any one of Embodiments G1 through G29 wherein a compound of Formula II-B is prepared using the method described in the Summary of the Invention or any one of Embodiments D1 through D31 comprising reducing a compound of Formula IV.

Embodiment H4. The process for preparing a compound of Formula I as described in the Summary of the Invention or any one of Embodiments G1 through G29 wherein a compound of Formula II-B is prepared using the method described in the Summary of the Invention or any one of Embodiments D1 through D31 comprising reducing a compound of Formula IV and the compound of Formula IV is prepared using the method as described in the Summary of the Invention or any one of Embodiments E1 through E27 comprising reacting a compound of Formula V or a salt thereof with a di-($C_1$-$C_4$ alkyl) malonate or a salt thereof.

Embodiment H5. The process of Embodiment H2 wherein the compound of Formula II-B is prepared by the process described in the Summary of the Invention or any one of Embodiments D1 through D31 comprising reducing a compound of Formula IV.

Embodiment H6. The process of Embodiment H5 wherein the compound of Formula IV is prepared by the process described in the Summary of the Invention or any one of Embodiments E1 through E27 comprising reducing a compound of Formula V or a salt thereof with a di-($C_1$-$C_4$ alkyl) malonate or a salt thereof.

Embodiment H7. The process for preparing a compound of Formula I wherein "prepared by the process" means "characterized by preparing a compound".

Embodiments of this invention, including any one of Embodiments $A^1$ through $A^{15}$, and C1 through C13 describing a compound, as well as Embodiments B1 through B16 (or B1 through B22), D1 through D31 (or D1 through D34), E1 through E27, F1 through F22, G1 through G29 (or G1 through G31), and H through H7 describing a process, as well as any other embodiments described herein, can be combined in any manner, and the descriptions of variables in the embodiments pertain not only to the compounds of Formulae II and IV but also to the starting compounds and intermediate compounds of Formulae II-A, II-B, III, IV, V and VI useful for preparing the compounds of Formulae I, II, and IV.

Combinations of Embodiments $A^1$ through $A^{15}$, and C1 through C13 describing a compound, as well as Embodiments B1 through B16 (or B1 through B22), D1 through D31 (or D1 through D34), E1 through E27, F1 through F22, G1 through G29 (or G1 through G31), and H1 through H7 describing the processes are illustrated by:

Embodiment 1A. A compound of Formula II and salts thereof as described in the Summary of the Invention wherein $R^1$ is methyl, ethyl or propyl; and $R^2$ is H or methyl.

Embodiment 1B. The process for preparing a compound Formula II-A as described in the Summary of the Invention wherein $R^1$ is $C_1$-$C_4$ alkyl comprising alkylating a compound of Formula III wherein the alkylating agent is a dialkylsulfate.

Embodiment 1C. A compound of Formula IV and salts thereof as described in the Summary of the Invention wherein $R^1$ is methyl, ethyl or propyl;

each $R^{3a}$ and $R^{3b}$ is independently methyl or ethyl; and $R^4$ is unsubstituted benzyl.

Embodiment 1D. The process for preparing a compound of Formula II-B as described in the Summary of the Invention wherein
$R^1$ is methyl, ethyl or propyl; and
$R^2$ is methyl, ethyl, n-propyl, i-propyl, n-butyl or t-butyl
comprising reducing a compound of Formula IV wherein
$R^1$ is methyl, ethyl or propyl;
each $R^{3a}$ and $R^{3b}$ is independently methyl or ethyl; and
$R^4$ is unsubstituted benzyl
wherein the reducing agent comprises a catalyst.

Embodiment 1E. The process for preparing a compound of Formula IV as described in the Summary of the Invention wherein
$R^1$ is methyl, ethyl or propyl;
each $R^{3a}$ and $R^{3b}$ is independently methyl, ethyl or propyl; and
$R^4$ is unsubstituted benzyl
comprising reacting a compound of Formula V or a salt thereof wherein
$R^1$ is methyl, ethyl or propyl; and
$R^4$ is unsubstituted benzyl
with a di-($C_1$-$C_4$ alkyl) malonate or a salt thereof selected from the group consisting of dimethyl malonate, diethyl malonate, diisopropyl malonate or di-n-propyl malonate or a sodium, lithium or potassium salt thereof.

Embodiment 1F. The process of preparing a compound of Formula I as described in the Summary of the Invention wherein
$R^1$ is methyl, ethyl or propyl
comprising contacting a compound of Formula II-A wherein
$R^1$ is methyl, ethyl or propyl
prepared by the process as described in the Summary of the Invention for preparing a compound of Formula II-A
with a compound of Formula VI.

Embodiment 1G. The process for preparing a compound of Formula I as described in the Summary of the Invention wherein
$R^1$ is methyl, ethyl or propyl
comprising contacting a compound of Formula II-B wherein
$R^1$ is methyl, ethyl or propyl; and
$R^2$ is methyl, ethyl, n-propyl, i-propyl, n-butyl or t-butyl
prepared by the process as described in the Summary of the Invention for preparing a compound of Formula II-B;
with a compound of Formula VI.

The compounds of Formulae I and IV can be prepared by general methods known in the art of synthetic organic chemistry. One or more of the following methods and variations as described in Schemes 1-11 can be used to prepare the compounds of Formula I and IV. The definitions of $A^1$, $A^2$, $A^3$, $R^1$, $R^2$, $R^{3a}$, $R^{3b}$, $B^1$, $B^2$ and $B^3$ in the compounds of Formulae II-A, II-B, III, IV, V and VI useful for preparing the compounds of Formula I, II, and IV below are as defined above in the Summary of the Invention unless otherwise noted.

As shown in Scheme 1 a compound of Formula I can be prepared by reaction of acids of Formula II-A (i.e. $R^2$ is H) with amines of Formula VI in the presence of a dehydrative coupling reagent such as propylphosphonic anhydride, dicyclohexylcarbodiimide, N-(3-dimethylaminopropyl)-N'-ethylcarbodiimide, N,N'-carbonyldiimidazole, 2-chloro-1,3-dimethylimidazolium chloride or 2-chloro-1-methylpyridinium iodide. Polymer-supported reagents, such as polymer-supported cyclohexylcarbodiimide, are also suitable. These reactions are typically run at temperatures ranging from 0-60° C. in a solvent such as dichloromethane, acetonitrile, N,N-dimethylformamide or ethyl acetate in the presence of a base such as triethylamine, N,N-diisopropylamine, or 1,8-diazabicyclo[5.4.0]undec-7-ene. See Organic Process Research & Development 2009, 13, 900-906 for coupling conditions employing propylphosphonic anhydride. Alternatively, a compound of Formula II-A (i.e. $R^2$ is H) can first be activated by preparing the acid chloride with a chlorinating reagent such as thionyl chloride. The activated intermediate can then be contacted with a compound Formula VI to prepare the compound of Formula I.

Scheme 1

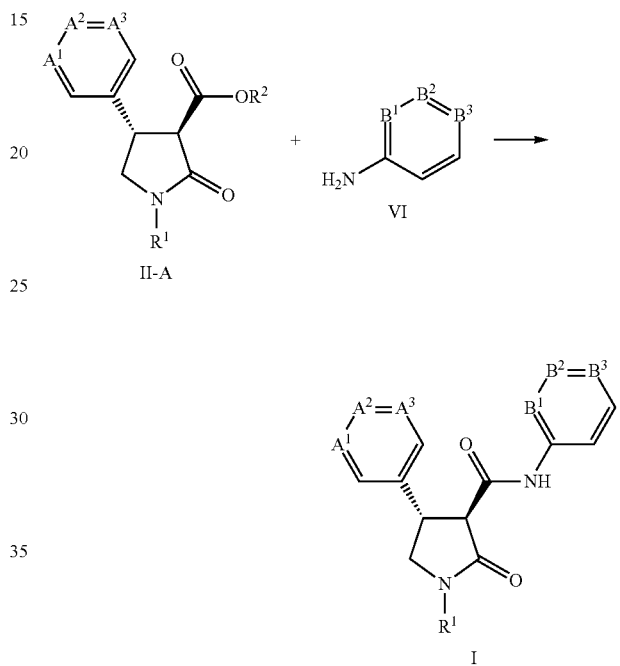

As shown in Scheme 2, a compound of Formula I can be obtained by heating a compound of Formula II-B (i.e. $R^2$ is $C_1$-$C_4$ alkyl) with amines of Formula VI in the absence or in the presence of organic solvent. The solvent can be either one or a combination of any two or three solvents, such as N,N-dimethylformamide, N,N-dimethylacetamide, dimethyl sulfoxide, N-methyl-2-pyrrolidinone, xylene, toluene, chlorobenzene. The temperature can be from 100° C. to 200° C. for 1 to 20 h, preferably in the range of 140° C. to 150° C. for 3 to 10 h.

Scheme 2

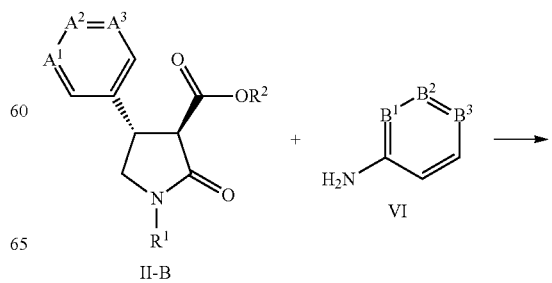

and lithium diisopropylamide in solvents such as tetrahydrofuran, toluene, isopropyl alcohol, acetonitrile and dichloromethane.

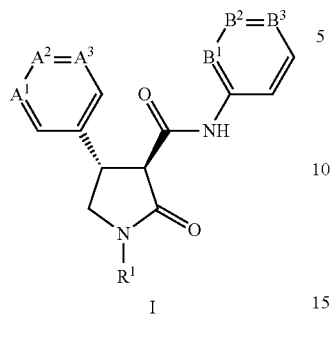

Of note is a compound of Formula I wherein $R^1$ is $CH_3$ and the remaining variables are defined below.

| Cmpd. No. | | M.P. ° C. |
|---|---|---|
| I-1 | $A^1$ is $CCF_3$, $A^2$ is CH, $A^3$ is CH, $B^1$ is CF, $B^2$ is CH and $B^3$ is CH | * |
| I-2 | $A^1$ is $CCF_3$, $A^2$ is CH, $A^3$ is CH, $B^1$ is CF, $B^2$ is N and $B^3$ is CF | 139-140 |
| I-3 | $A^1$ is N, $A^2$ is $CCF_3$, $A^3$ is CH, $B^1$ is CF, $B^2$ is CF and $B^3$ is CH | * |
| I-4 | $A^1$ is $CCH_3$, $A^2$ is N, $A^3$ is $COCHF_2$, $B^1$ is CF, $B^2$ is CF and $B^3$ is CH | * |
| I-5 | $A^1$ is CH, $A^2$ is $CCF_3$, $A^3$ is CH, $B^1$ is CF, $B^2$ is CF and $B^3$ is CH | 164-165.7 |
| I-6 | $A^1$ is CH, $A^2$ is $CCF_3$, $A^3$ is CH, $B^1$ is CF, $B^2$ is N and $B^3$ is CF | * |

* See Synthesis Examples for $^1$H NMR data.

Esters of Formula II-B can be hydrolyzed to an acid of Formula II-A of esters of Formula 4 by methods well known to those skilled in the art. This hydrolysis can be carried out with aqueous base or aqueous acid, typically in the presence of a co-solvent. Suitable bases for the reaction include, but are not limited to, hydroxides such as sodium and potassium hydroxide and carbonates such as sodium and potassium carbonate. Suitable acids for the reaction include, but are not limited to, inorganic acids such as hydrochloric acid, hydrobromic acid and sulfuric acid, and organic acids such as acetic acid and trifluoroacetic acid. A wide variety of co-solvents are suitable for the reaction including, but not limited to, methanol, ethanol and tetrahydrofuran. The reaction is conducted at temperatures ranging from −20° C. to the boiling point of the solvent, and typically from 0 to 100° C.

As shown in Scheme 3, a compound of Formula II-A can be prepared by reacting compounds of Formula III with an alkylating reagent in presence of a base. Suitable methylating reagents for the reaction include alkyl halides, dialkyl sulfates, dialkyl carbonates, or trialkyl phosphates. Suitable bases for the reaction include alkali metal hydrides such as sodium hydride; or alkali metal alkoxides such as sodium isopropoxide and potassium tert-butoxide; or alkali metal hydroxides such as potassium hydroxide and sodium hydroxide; or alkali metal carbonates such as potassium carbonate and cesium carbonate; or bases such as lithium bis(trimethylsilyl)amide, sodium bis(trimethylsilyl)amide Scheme 3

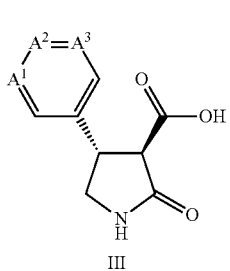

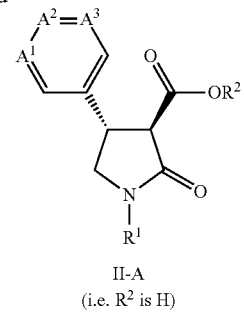

Of note is a compound of Formula II-A wherein $R^1$ is $CH_3$ and the remaining variables are defined below.

| Cmpd. No. | | M.P. ° C. |
|---|---|---|
| II-A-1 | $A^1$ is $CCF_3$, $A^2$ is CH and $A^3$ is CH | * |
| II-A-3 | $A^1$ is CH, $A^2$ is $CCF_3$ and $A^3$ is CH | 158-164 |

* See Synthesis Example for $^1$H NMR data.

As shown in Scheme 4, a compound of Formula II-B can be obtained by the reduction of a compound of Formula IV and subsequent in situ cyclization of the resulting intermediate amine. Methods for removing the benzyl group from a compound of Formula IV are known in the literature, including catalytic hydrogenation in the presence of palladium on carbon, reduction using Raney nickel or transfer hydrogenation (see, for example, *Bull. Chen. Soc. Japan* 2004, 77(7), 1405-1406, and *Synthesis* 1987, 1, 53-55).

Scheme 4

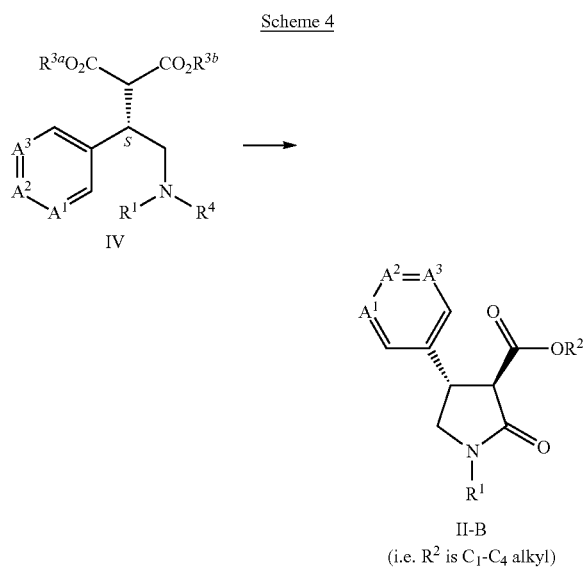

Of note is a compound of Formula II-B wherein $R^1$ is $CH_3$ and the remaining variables are defined below.

| Cmpd. No. | | M.P. °C. (or M.S) |
|---|---|---|
| II-B-1 | $A^1$ is $CCF_3$, $A^2$ is CH, $A^3$ is CH and $R^2$ is $CH_3$ | * |
| II-B-3 | $A^1$ is N, $A^2$ is $CCF_3$, $A^3$ is CH and $R^2$ is $CH_3$ | * |
| II-B-5 | $A^1$ is CH, $A^2$ is $CCF_3$, $A^3$ is CH and $R^2$ is $CH_2CH_3$ | 316 |

* See Synthesis Examples for $^1H$ NMR data.

As shown in Scheme 5, a compound of Formula IV can be prepared by reacting the chloro compound of Formula V with malonate alkali salt, such as potassium, sodium, lithium or cesium salt, in an organic solvent, such as N,N-dimethylformamide, N,N-dimethylacetamide, dimethyl sulfoxide, N-methyl-2-pyrrolidinone, acetonitrile. The malonate alkali salt can be generated in situ by the reaction of a di-($C_1$-$C_4$ alkyl) malonate with an inorganic base, such as, but not limited to, potassium carbonate, sodium carbonate or cesium carbonate. Typically, the reaction is carried out at a temperature from about 15° C. to about 60° C., preferably at about 25° C.

Scheme 5

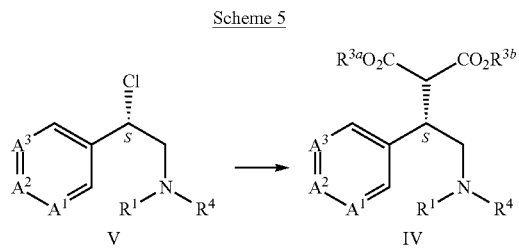

Of note is a compound of Formula IV wherein $R^1$ is $CH_3$, $R^{3a}$ is $CH_3$, $R^{3b}$ is $CH_3$, $R^4$ is $CH_2Ph$ (i.e. unsubstituted benzyl) and the remaining variables are defined below.

| Cmpd. No. | | M.P. °C. |
|---|---|---|
| IV-1 | $A^1$ is $CCF_3$, $A^2$ is CH and $A^3$ is CH | * |
| IV-3 | $A^1$ is N, $A^2$ is $CCF_3$ and $A^3$ is CH | * |
| IV-4 | $A^1$ is $CCH_3$, $A^2$ is N and $A^3$ is $COCHF_2$ | * |
| IV-5 | $A^1$ is CH, $A^2$ is $CCF_3$ and $A^3$ is CH | * |

* See Synthesis Examples for $^1H$ NMR data.

As shown in Scheme 6, a compound of Formula V can be prepared by treatment of an aminoalcohol of Formula VII-A with a chlorinating reagent, such as, but not limited to, thionyl chloride or oxalyl chloride. Generally, the reaction can be conducted in a solvent, such as, but not limited to, ethylene chloride, 1,2-dichloroethane, toluene, ethyl acetate, acetonitrile or tetrahydrofuran at a temperature ranging from 0° C. to 40° C. with 1 to 2 eq. of chlorination reagent. Alternatively, a compound of Formula V can be prepared by reaction of aminoalcohol of Formula VII-B with methanesulfonyl chloride, benzenesulfonyl chloride, or p-toluenesulfonyl chloride, o-toluenesulfonyl chloride, m-toluenesulfonyl chloride in the presence of a base. Suitable bases for this reaction include, but are not limited to, piperidine, morpholine or triethyl amine, pyridine or N,N-diisopropylethylamine. The solvents can be, but are not limited to, ethylene chloride, 1,2-dichloroethane, toluene, ethyl acetate, acetonitrile or tetrahydrofuran. Typically, the reaction is conducted at a temperature ranging from 0° C. to 40° C. using 1 to 4 eq. of chlorination reagent.

Scheme 6

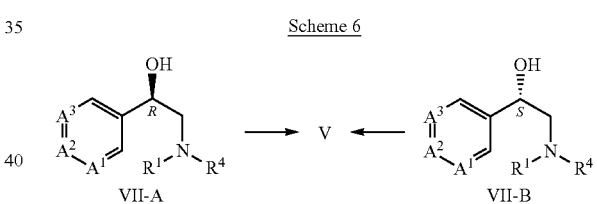

As shown in Scheme 7, a compound of Formula VII-A can be prepared by reaction of an epoxide (i.e. oxirane) of Formula VIII with an amine of Formula IX. Typically, the reaction is carried out at a temperature from about 80° C. to 160° C. neat. The reaction also can be conducted in solvents, such as, acetonitrile, toluene, xylene, mesitylene, N,N-dimethylformamide, NN-dimethylacetamide, dimethyl sulfoxide and N-methyl-2-pyrrolidinone at temperatures ranging from about 80° C. to 160° C. The amine of Formula IX can be used from 1 to 5 eq. relative to epoxide (i.e. oxirane) of Formula VIII, preferably about 1.1 eq. Alternatively, a compound of Formula VII-A can be prepared by asymmetric reduction of α-aminoketones of Formula X or their hydrochloric, hydrobromic, or trifluoroacetic salt forms. It is recognized by one skilled in the art that such asymmetric reduction can be carried out by hydrogenation in the presence of a catalyst. Suitable catalysts for this reaction include ruthenium-based systems (see, *J. Am. Chem. Soc.* 1988, 110, 629-631; *J. Am. Chem. Soc.* 2000, 122, 6510-6511; *Tetrahedron: Asymmetry*, 2010, 2479-2486), and rhodium-based systems (see, *J. Am. Chem. Soc.* 1990, 112, 5876-5878).

Scheme 7

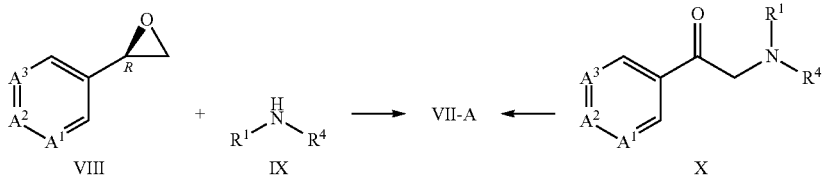

It is recognized by one skilled in the art that the enantiomeric compound of Formula VII-B can be prepared by treating the (S)-enantiomer of Formula VIII with amines of Formula IX, as well as by asymmetric reduction of α-aminoketones of Formula X.

As shown in Scheme 8, a compound of Formula VIII can be prepared by asymmetric reduction of α-halomethyl ketone of Formula XI (wherein X is Cl or Br) followed by cyclization in situ after treatment with a base. It is recognized by one skilled in the art that the asymmetric reduction can be carried out by asymmetric transfer hydrogenation in the presence of formic acid or formate as the hydrogen source (see, *J. Am. Chem. Soc.* 1996, 118, 2521-2522; *J. Org. Chem.* 2005, 70, 3188-3197; *Org. Lett.* 2002, 4, 4373-4376; *Tetrahedron* 2004, 60, 7411-7417), or hydrogenation in the presence of hydrogen (gas) as the hydrogen source (see, *J. Am. Chem. Soc.* 2011, 133, 14960-14963; *Org Lett* 2007, 9, 255).

Scheme 8

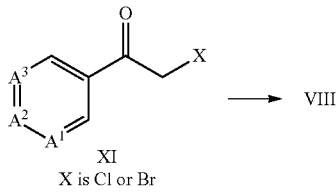

As shown in Scheme 9, a compound of Formula X can be prepared by the reaction of α-halomethyl ketone of Formula XI with an amine of Formula IX in a solvent, such as, but not limited to, acetone, ethyl acetate, acetonitrile, toluene, xylene, mesitylene, N,N-dimethylformamide, N,N-dimethylacetamide, dimethyl sulfoxide or N-methyl-2-pyrrolidinone at about 20° C. to 130° C., preferably at 20° C. to 60° C. The amine of Formula IX can be used in an amount from about 1 to about 5 eq., preferably 1.1 eq.

Scheme 9

As shown in Scheme 10, a compound of Formula XI can be prepared by halogenation of methylketone of Formula XII via a chlorinating reagent. The chlorinating reagent can be N-chlorosuccinimide, chlorine, sulfuryl chloride, isocyanuric chloride, oxone in the presence of ammonium chloride, or potassium persulfate in the presence of sodium chloride. It is recognized by one skilled in the art that a compound of Formula XI can be prepared by reaction of the bromo compound of Formula XIII with magnesium metal, diisopropylmagnesium chloride, or diisopropylmagnesium bromide to form an arylmagnesium compound followed by reaction with N-methoxyl-N-methylchloroacetamide (see, *Tetrahedron* 2003, 59, 1317-1325). Alternatively, a compound of Formula XI can be prepared via reacting a compound of Formula XIII with n-butyllithium at −30° C. to −78° C., preferably, at −60° C. to −78° C., followed by quenching the aryllithium intermediate generated in situ by N-methoxyl-N-methylchloroacetamide at −78° C. to 0° C. in a solvent such as, tetrahydrofuran, diethylether, tert-butyl methyl ether, 1,4-dioxane, preferable in tert-butylmethylether.

Scheme 10

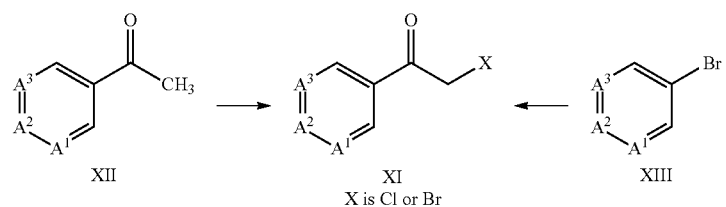

Of note is a compound of Formula XI wherein the variables are defined below.

| Cmpd. No. | | M.S. |
|---|---|---|
| XI-3 | $A^1$ is N, $A^2$ is $CCF_3$, $A^3$ is CH and X is Br | 316 |
| XI-4 | $A^1$ is $CCH_3$, $A^2$ is N, $A^3$ is $COCHF_2$ and X is Br | * |
| IV-5 | $A^1$ is CH, $A^2$ is $CCF_3$, $A^3$ is CH and X is Cl | * |

* See Synthesis Examples for $^1H$ NMR data.

As shown in Scheme 11, a compound of Formula II-B can be prepared by two sequential alkylations of a compound of Formula III. In this method, a compound of II-A is prepared using the conditions described above for Scheme 3 (N-alkylation) followed by in-situ alkylation with a second alkylating agent to prepare a compound of Formula II-B (O-alkylation). This sequence is alternatively known as a "two-step, one-pot" reaction. Conditions for facilitating O-alkylation include contacting the prepared compound of Formula II-A with sufficient dimethylsulfate ($R^2$ is Me) or diethylsulfate ($R^2$ is Et) and additional base (e.g., potassium carbonate) to prepare a compound of Formula II-B. Alternatively, O-alkylation can be achieved under acidic conditions by contacting the prepared compound of Formula II-A with acid (e.g., sulfuric acid) and additional methanol ($R^2$ is Me) or ethanol ($R^2$ is Et). Appropriate solvents for the "two-step, one-pot" reaction are the same as those listed for the preparation of the compound of Formula II-A in Scheme 3.

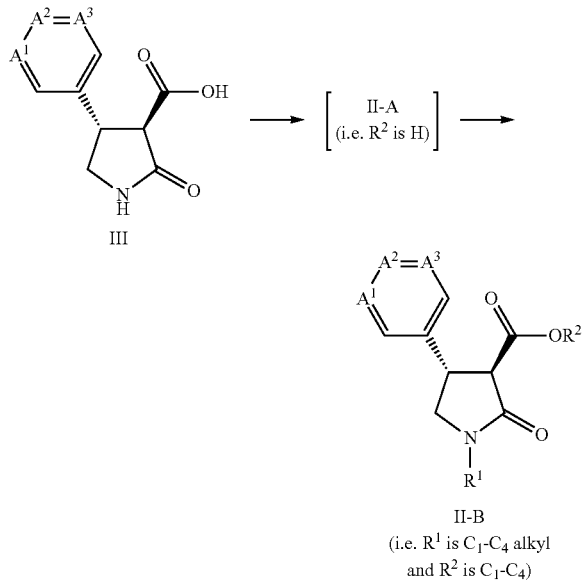

Scheme 11

It is recognized by one skilled in the art that various functional groups can be converted into others to provide different compounds of Formula I. For a valuable resource that illustrates the interconversion of functional groups in a simple and straightforward fashion, see Larock, R. C., *Comprehensive Organic Transformations: A Guide to Functional Group Preparations,* 2nd Ed., Wiley-VCH, New York, 1999.

It is recognized that some reagents and reaction conditions described above for preparing compounds of Formula I may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis,* 2nd ed.; Wiley: New York, 1991). One skilled in the art will recognize that, in some cases, after the introduction of a given reagent as it is depicted in any individual Scheme, it may be necessary to perform additional routine synthetic steps not described in detail to complete the synthesis of compounds of Formula I. One skilled in the art will also recognize that it may be necessary to perform a combination of the steps illustrated in the above Schemes in an order other than that implied by the particular presented to prepare the compounds of Formula I.

One skilled in the art will also recognize that compounds of Formula I and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1H$ NMR spectra are reported in ppm downfield from tetramethylsilane in $CDCl_3$ solution at 500 MHz unless indicated otherwise; "s" means singlet, "d" means doublet, "dd" means doublet of doublets, "t" means triplet, "q" means quartet, "m" means multiplet, "br t" means broad triplet, "br d" means broad doublet and "br s" means broad singlet. The enentiomeric excess (e.e.) was calculated from the enantiomeric ratio (ER) as determined by chiral high performance liquid chromatography (HPLC) analysis using a Chiralpak® AD-H or Chiralpak© AS (oxiranes) column eluting with a mixture of hexanes/isopropanol (ranging from 85:15 to 99:1) at a flow rate ranging from 1.0 to 1.5 mL/min with a colunm temperature of 30° C.

Synthesis Example 1

Preparation of (3S,4S)-N-(2-fluorophenyl)-1-methyl-2-oxo-4-[3-(trifluoromethyl)phenyl]-3-pyrrolidinecarboxamide Step A: Preparation of (3R,4S)-1-methyl-2-oxo-4-[3-(trifluoromethyl)phenyl]-3-pyrrolidinecarboxylic acid Dimethylsulfate (57.6 g, 0.458 mol) was added dropwise into a mixture of (3R,4S)-2-oxo-4-[3-(trifluoromethyl)phenyl]-3-pyrrolidinecarboxylic acid (50 g, 0.183 mol) and potassium hydroxide (34.2 g, 0.549 mol) in isopropyl alcohol (350 mL) at 20° C. The reaction mixture was stirred for 1 h at 20° C., and quenched with water (200 mL). The resulting solution was concentrated under reduced pressure to remove excess isopropyl alcohol, then acidified with concentrated hydrochloric acid and extracted with dichloromethane (2×200 mL). Concentration and crystallization from tert-butyl methyl ether/heptane afforded the title compound as an off-white solid (37 g, 0.132 mol, 93% e.e.).

$^1$H NMR (400 MHz, dmso-d$_6$) δ 2.81 (s, 3H), 3.40 (dd, 1H), 3.64 (d, 1H), 3.76 (dd, 1H), 3.97 (dd, 1H), 7.70-7.58 (m, 3H), 7.76 (s, 1H), 12.83 (br s, 1H). M.P.=93.1° C.

Step B: Preparation of (3S,4S)-N-(2-fluorophenyl)-1-methyl-2-oxo-4-[3-(trifluoromethyl)phenyl]-3-pyrrolidinecarboxamide To a dichloromethane (600 mL) solution of (3R,4S)-1-methyl-2-oxo-4-[3-(trifluoromethyl)phenyl]-3-pyrrolidinecarboxylic acid (i.e. the product obtained in Step A) (150 g, 0.522 mol) were added triethylamine (57.1 g, 0.564 mol) and methanesulfonyl chloride (62.8 g, 0.548 mol) dropwise while the temperature was maintained below 10° C. The resulting mixture was stirred at 5° C. for 1 h, then 2-fluoroaniline (60.9 g, 0.548 mol) was added dropwise at a temperature below 10° C. The reaction mixture was stirred at 5° C. for 30 min, then triethylamine (57.1 g, 0.564 mol) was added dropwise at a temperature below 10° C. After stirring at 15° C. for 1 h, the reaction was quenched with 1 N aqueous hydrochloric acid solution (600 mL), and the organic layer was collected. The organic layer was then washed with saturated aqueous sodium bicarbonate solution (600 mL) followed by water (600 mL). Concentration under reduced pressure and crystallization from isopropyl alcohol afforded the title compound as a white crystalline solid (149 g, 0.392 mol, 99% e.e.).

$^1$H NMR (dmso-d$_6$) δ 2.85 (s, 3H), 3.50-3.44 (m, 1H), 3.84-3.79 (m, 1H), 4.10-4.04 (m, 2H), 7.18-7.12 (m, 2H), 7.28-7.24 (m, 1H), 7.66-7.59 (m, 2H), 7.70-7.69 (m, 1H), 7.76 (s, 1H), 8.00-7.97 (m, 1H), 10.13 (s, 1H). M.P.=141.9° C.

Synthesis Example 2

Alternate Preparation of (3S,4S)-N-(2-fluorophenyl)-1-methyl-2-oxo-4-[3-(trifluoromethyl)phenyl]-3-pyrrolidinecarboxamide Step A: Preparation of 2-[methyl(phenylmethyl)amino]-1-[3-(trifluoromethyl)phenyl]-ethanone 1:1 hydrochloride To a solution of 2-bromo-1-[3-(trifluoromethyl)phenyl]-ethanone (8.6 g, 32.2 mmol) and N-methyl-benzenemethanamine (3.7 g, 30.6 mmol) in dichloromethane (300 mL) was added potassium carbonate (8.9 g, 64.4 mmol) and the resulting mixture was stirred at room temperature for 5 h. Water (20 mL) was added and stirred for an additional 3 h. The organic layer was separated, washed with brine, dried over MgSO$_4$, filtered and concentrated under reduced pressure to yield a light yellow oil. The crude oil was diluted with diethyl ether (100 mL), and a solution of aqueous hydrochloric acid in diethyl ether (15 mL, 2 M) was added over 10 min at room temperature. The resulting white slurry was filtered, washed with diethyl ether (20 mL), and suction-dried to provide the title product as a white solid (9.2 g).

$^1$H NMR (dmso-d$_6$) δ 2.81 (br s, 3H), 4.29 (br s, 1H), 4.47-4.52 (m, 1H), 5.07-5.16 (m, 2H), 7.48 (br s, 3H), 7.62 (br s, 2H), 7.88 (br t, 1H), 8.14 (br d, 1H), 8.27 (d, 2H), 10.39 (br s, 1H).

Step B Preparation of (αS)-α-[[methyl(phenylmethyl)amino]methyl]-3-(trifluoromethyl)benzenemethanol To an autoclave reactor charged with 2-[methyl(phenylmethyl)amino]-1-[3-(trifluoromethyl)phenyl]-ethanone 1:1 hydrochloride (i.e. the product obtained in Step A) (1.57 g, 4.57 mmol), isopropyl alcohol (40 mL), potassium hydroxide (1.8 mL, 5 M in H$_2$O) was added dichloro[(R)-(+)-2,2',6,6'-tetramethoxy-4,4'-bis(di(3,5-xylyl)phosphino)-3,3'-bipyridine][(1R,2R)-(+)-1,2-diphenylethylenediamine]ruthenium (II) (CAS Registry No. 478308-93-9) (2.3 mg, 0.0018 mmol). The mixture was degassed by five cycles of pressuring with nitrogen 1,379 kPa (200 psi) and releasing, followed by three cycles of pressuring with hydrogen 1,379 kPa (200 psi) and releasing, then 2758 kPa (400 psi) of hydrogen was pressured in and stirred at 60° C. for 1 h. Hydrogen was released and the reaction mixture was concentrated under reduced pressure, diluted with ethyl acetate (50 mL), then washed with water (50 mL) and brine, dried over MgSO$_4$, filtered and concentrated to provide the title product as a light brown oil (1.3 g, 98% e.e.).

$^1$H NMR δ 2.34 (s, 3H), 2.56 (m, 2H), 3.56 (d, 1H), 3.76 (d, 1H), 4.78 (dd, 1H), 7.29-7.37 (m, 5H), 7.44 (t, 1H), 7.53 (d, 2H), 7.62 (s, 1H).

The enantiomer, (αR)-α-[[methyl(phenylmethyl)amino]methyl]-3-(trifluoromethyl)benzenemethanol, was prepared similarly using dichloro[(S)-(−)-2,2',6,6'-tetramethoxy-4,4'-bis(di(3,5-xylyl)phosphino)-3,3'-bipyridine][(1S,2S)-(−)-1,2-diphenylethylenediamine]ruthenium (II) (CAS Registry No. 821793-37-7) as the catalyst.

Step C Preparation of (βS)-β-chloro-N-methyl-N-(phenylmethyl)-3-(trifluoromethyl)benzeneethanamine To an ice-cooled solution of (αR)-α-[[methyl(phenylmethyl)amino]methyl]-3-(trifluoromethyl)benzenemethanol (i.e. the product obtained in Step B) (5.6 g, 18 mmol) in dichloromethane (100 mL) at 5° C.) was added thionyl chloride (2.3 g, 19.3 mmol) over 2 min. After completion of addition, the ice bath was removed and the yellow mixture was stirred at 23° C. for 3 h, then quenched with saturated aqueous sodium bicarbonate (50 mL), the organic layer was separated, washed with brine, dried over MgSO$_4$, filtered, and concentrated to provide the title product as an orange oil (6.2 g), which was used directly in the next step.

Alternate Preparation: To an ice-cooled solution of (αS)-α-[[methyl(phenylmethyl)amino]methyl]-3-(trifluoromethyl)benzenemethanol (16 g, 52 mmol) in dichloromethane (180 mL) (10° C.) added methanesulfonyl chloride (13.4 g, 117 mmol) over 2 min, followed by triethylamine (18 mL, 129 mmol) over 5 min. After completion of addition, the ice bath was removed and the yellow mixture was stirred at 23° C. for 2 h, then quenched with saturated sodium bicarbonate solution (100 mL), the organic layer was separated, washed with brine, dried over MgSO$_4$, filtered, and concentrated to provide the title product as an orange oil (18 g).

$^1$H NMR δ 2.29 (s, 3H), 2.96 (m, 2H), 3.49 (d, 1H), 3.60 (d, 1H), 4.91 (t, 1H), 7.13 (m, 2H), 7.24 (m, 3H), 7.46 (m, 2H), 7.56 (m, 2H).

Step D: Preparation of 1,3-dimethyl 2-[(1S)-2-[methyl(phenylmethyl)amino]-1-[3-(trifluoromethyl)phenyl]ethyl]propanedioate To a solution of (βS)-β-chloro-N-methyl-N-(phenylmethyl)-3-(trifluoromethyl)benzeneethanamnine (6.2 g crude orange oil from Step C) in acetonitrile (100 mL) added dimethyl malonate (2.8 g, 22.7 mmol) and potassium carbonate (5 g) at ambient temperature. The mixture was stirred at 25° C. for 24 h, diluted with saturated aqueous ammonium chloride (50 mL), and extracted with ethyl acetate (30 mL), the organic layer was separated and concentrated under reduced pressure to provide a light yellow oil (8.2 g). The crude oil was crystallized from methanol/water (40 mL:10 mL) to provide the title product (5 g, 97% e.e.) as a white solid.

$^1$H NMR δ 2.18 (s, 3H), 2.60 (dd, 1H), 2.70 (dd, 1H), 3.40 (d, 1H), 3.44 (s, 3H), 3.55 (d, 1H), 3.72 (s, 3H), 3.73 (m, 1H), 3.77 (m, 1H), 7.12 (m, 2H), 7.22-7.27 (m, 3H), 7.36-7.40 (m, 3H), 7.48 (d, 1H).

Step E: Preparation of methyl (3R,4S)-1-methyl-2-oxo-4-[3-(trifluoromethyl)phenyl]-3-pyrrolidinecarboxylate To a 500 mL Parr shaker added 1,3-dimethyl 2-[(1S)-2-[methyl(phenylmethyl)amino]-1-[3-(trifluoromethyl)phenyl]ethyl]propanedioate (i.e. the product obtained in Step D) (8.1 g, 19.1 mmol), methanol (50 mL) and 10% palladium on carbon (2.0 g, containing ~50% water). The mixture was degassed by 5 cycles of pressuring hydrogen 345 kPa (50 psi) and releasing, then shaken for 6 h under hydrogen 345 kPa (50 psi) at 24° C. The mixture was filtered to remove palladium on carbon, the filtrate was concentrated under reduced pressure to provide the title product as a white solid (5.8 g, 97% e.e.).

$^1$H NMR δ 2.96 (s, 3H), 3.44 (dd, 1H), 3.58 (d, 1H), 3.79 (s, 3H), 3.83 (t, 1H), 4.08 (q, 1H), 7.43 (d, 1H), 7.48 (m, 2H), 7.56 (d, 1H).

Step F: Preparation of (3S,4S)-N-(2-fluorophenyl)-1-methyl-2-oxo-4-[3-(trifluoromethyl)phenyl]-3-pyrrolidinecarboxamide The mixture of methyl (3R,4S)-1-methyl-2-oxo-4-[3-(trifluoromethyl)phenyl]-3-pyrrolidinecarboxylate (i.e. the product obtained in Step E) (5.8 g, 19.2 mmol), 2-fluoroaniline (2.6 g, 23 mmol) and xylene (50 mL) was heated to the reflux temperature for 12 h, while the methanol generated was distilled out to maintain the pot temperature at 142° C. The progress of reaction was monitored by HPLC until the conversion was greater than 97%. The mixture was concentrated to about 15 mL via distillation, after cooling to 50° C., hexanes (60 mL) was added, and the mixture was cooled to 2° C. via an ice bath. The slurry was filtered, and the resulting filter cake was rinsed with hexanes (30 mL), dried under vacuum to afford the title product (6.6 g, 97% e.e.) as an off-white solid.

$^1$H NMR δ 3.02 (s, 3H), 3.47 (dd, 1H), 3.64 (d, 1H), 3.82 (t, 1H), 4.19 (q, 1H), 7.04-7.10 (m, 3H), 7.50-7.61 (m, 4H), 8.23 (dt, 1H), 9.90 (br s, 1H).

Alternate Preparation: To a solution of methyl (3R,4S)-1-methyl-2-oxo-4-[3-(trifluoromethyl)phenyl]-3-pyrrolidinecarboxylate (i.e. the product obtained in Step E) (2.55 g, 8.4 mmol) in methanol (30 mL) added water (10 mL), followed by 4 N aqueous sodium hydroxide (20 mL) at room temperature, the resulting mixture was stirred at room temperature for 2 h. The mixture was concentrated to about 20 mL under reduced pressure, then cooled in an ice bath, and acidified with 1 N aqueous hydrochloric acid to pH=2. The resulting slurry was extracted with ethyl acetate (50 mL), dried over MgSO$_4$, filtered and concentrated to yield 2.5 g of a white solid. The solid was dissolved in dichloromethane (30 mL), and N,N-dimethylformamide (2 drops) and oxalyl chloride (1.0 mL) was added, the resulting mixture was stirred for 1 h at room temperature, then concentrated under reduced pressure to provide a light yellow solid. To this yellow solid was added dichloromethane (50 mL), potassium carbonate (2 g) and 2-fluoroaniline (0.9 mL), the resulting mixture was stirred for 30 min at room temperature, then washed with water (50 mL) and brine, dried over MgSO$_4$, filtered and concentrated under reduced pressure to provide an off-white solid, which was recrystallized from hexanes/ethyl acetate (100 mL to 5 mL) to provide title product (2.38 g, 97% e.e.) as a white solid.

Synthesis Example 3

Preparation of (3S,4S)-N-(2,6-difluoro-3-pyridinyl)-1-methyl-2-oxo-4-[4-(trifluoromethyl)phenyl]-3-pyrrolidinecarboxamide Step A: Preparation of (2R)-2-[4-(trifluoromethyl)phenyl]oxirane To a mixture of 2-chloro-1-[4-(trifluoromethyl)phenyl]-ethanone (22 g, 98.8 mmol)), acetonitrile (85 mL) and [N-(1[N-[(1S,2S)-2-(amino-κN)-1,2-diphenylethyl]-4-methylbenzenesulfonamidato-κN]chloro[(1,2,3,4,5,6-η)-1,3,5-trimethylbenzene]-ruthenium (CAS Registry No. 174813-81-1, 123 mg, 0.198 mmol) was added a solution of sodium formate (30.3 g, 494 mmol) in water (85 mL). The resulting mixture was stirred at 40° C. for 3.5 h, then 4 N aqueous sodium hydroxide (50 mL) was added and stirred at room temperature for 5 h. The organic layer was separated and concentrated under reduced pressure to yield a brown oil, which was purified via column chromatoagraphy to afford the title compound as a clear oil (16 g, 94% e.e.).

$^1$H NMR δ 2.78 (dd, 1H), 3.19 (dd, 1H), 3.92 (m, 1H), 7.40 (d, 2H), 7.61 (d, 2H).

Step B: Preparation of (βS)-β-chloro-N-methyl-N-(phenylmethyl)-4-(trifluoromethyl) benzeneethanamine The mixture of (2R)-2-[4-(trifluoromethyl)phenyl]oxirane (i.e. the product obtained in Step A) (36.4 g, 193 mmol) and N-methyl-benzenemethanamine (23.5 g, 193 mmol) was stirred at 100° C. for 3 h (the progress was monitored by HPLC), after cooling to room temperature, dichloromethane (400 mL) was added, and the mixture was cooled in an ice bath to 5° C., then thionyl chloride (24.2 g, 203 mmol) was added over 20 min. The ice bath was removed, and the reaction mixture was stirred at ambient temperature (23° C.) for 5 h. The resulting yellow solution was poured into ice-water (400 mL). The organic layer was separated, washed with saturated aqueous sodium bicarbonate, dried over MgSO$_4$, filtered and concentrated under reduced pressure to provide the title compound (51 g) as a light brown oil.

$^1$H NMR δ 2.30 (s, 3H), 2.96 (m, 2H), 3.49-3.60 (dd, 2H), 4.90 (t, 1H), 7.12 (m, 2H), 7.23-7.29 (m, 3H), 7.40 (d, 2H), 7.58 (d, 2H).

Step C Preparation of 1,3-dimethyl 2-[(1S)-2-[methyl(phenylmethyl)amino]-1-[4-(trifluoromethyl)phenyl]ethyl]propanedioate To a solution of (βS)-β-chloro-N-methyl-N-(phenylmethyl)-4-(trifluoromethyl) benzeneethanamine (i.e. the product obtained in Step B) (36 g crude light brown oil, 110 mmol) in acetonitrile (500 mL) was added dimethyl malonate (17.4 g, 132 mmol) and potassium carbonate (22.8 g, 165 mmol) at ambient temperature, and stirred at 25° C. for 24 h. The mixture was diluted with saturated aqueous ammonium chloride (300 mL), extracted with ethyl acetate (300 mL), the organic layer was separated and concentrated under reduced pressure to provide a light yellow oil which was purified by column chromatography to provide title product (40 g) as a light yellow solid.

$^1$H NMR δ 2.19 (s, 3H), 2.57 (dd, 1H), 2.68 (dd, 1H), 3.39 (d, 1H), 3.45 (s, 3H), 3.53 (d, 1H) 3.71 (d, 1H), 3.73 (s, 3H), 3.77 (m, 1H), 7.10 (m, 2H), 7.22-7.28 (m, 5H), 7.52 (d, 2H).

Step D: Preparation of methyl (3R,4S)-1-methyl-2-oxo-4-[(trifluoromethyl)phenyl]-3-pyrrolidinecarboxylate To a 500 mL Parr shaker added 1,3-dimethyl 2-[(1S)-2-[methyl(phenylmethyl)amino]-1-[4-(trifluoromethyl)phenyl]ethyl]propanedioate (i.e. the product obtained in Step C) (44 g 104 mmol), methanol (300 mL) and 10% palladium on carbon (8.0 g, containing ~50% water). The mixture was degassed by 5 cycles of pressuring hydrogen 345 kPa (50 psi) and releasing, then shaken for 6 h under hydrogen 345 kPa (50 psi) at 24° C. The mixture was filtered to remove palladium on carbon and the filtrate was concentrated under reduced pressure to provide the title product as a white solid (29 g, 97% e.e.).

$^1$H NMR δ 2.96 (s, 3H), 3.42 (dd, 1H), 3.57 (d, 1H), 3.79 (s, 3H), 3.83 (dd, 1H), 4.07 (q, 1H), 7.35 (d, 2H), 7.61 (d, 2H)

Step E: Preparation of (3S,4S)-N-(2,6-difluoro-3-pyridinyl)-1-methyl-2-oxo-4-[4-(trifluoromethyl)phenyl]-3-pyrrolidinecarboxamide The mixture of methyl (3R,4S)-1-methyl-2-oxo-4-[4-(trifluoromethyl)phenyl]-3-pyrrolidinecarboxylate (i.e. the product obtained in Step D above) (5 g, 16.6 mmol), 2,6-difluoropyridin-3-amine (2.37 g, 18.2 mmol) and xylene (45 mL) was heated to the reflux temperature (142° C.) for 10 h, while the methanol generated was distilled out to maintain the pot temperature at 142° C. The progress of reaction was monitored by HPLC until the conversion was greater than 97%. The mixture was concentrated under reduced pressure and purified by silica gel column chromatography, eluting with 35% ethyl acetate in hexanes to provide 5.88 g of an off-white solid, which was recrystallized from a mixture of n-chlorobutane (50 mL) and hexanes 75 mL to afford the title product (2.3 g, 99.8% e.e.) as white solid.

$^1$H NMR δ 3.02 (s, 3H), 3.48 (dd, 1H), 3.64 (d, 1H), 3.81 (dd, 1H), 4.12 (q, 1H), 6.78 (dd, 1H), 7.49 (d, 2H), 7.65 (d, 2H), 8.72 (m, 1H), 10.07 (s, 1H).

Synthesis Example 4

Preparation of (3S,4S)-N-(2,3-difluorophenyl)-1-methyl-2-oxo-4-[6-(trifluoromethyl)-3-pyridinyl]-3-pyrrolidinecarboxamide

Step A Preparation of 2-chloro-1-[6-(trifluoromethyl)-3-pyridinyl]ethanone

To a cooled (−76° C.) solution of 5-bromo-2-(trifluoromethyl)pyridine (20.3 g, 90 mmol) in tert-butyl methyl ether (500 mL) was added an n-butyllithium solution (50 mL, 2 M in cyclohexane) over 40 min. The resulting light brown solution stirred for 30 min while the temperature was maintained at −76° C. to −72° C. in a dry ice-acetone bath. A solution of 2-chloro-N-methoxy-N-methylacetamide (14.1 g, 103 mmol) in tert-butyl methyl ether (100 mL) was added over 30 min at −70° C. to −73° C., the resulting mixture was warmed to 5° C. over 1 h, then quenched with saturated aqueous ammonium hydrochloride solution (300 mL), the organic layer was separated, dried over MgSO$_4$, filtered and concentrated under reduced pressure to provide the title compound as an orange oil (24 g).

$^1$H NMR δ 4.70 (s, 2H), 7.87 (d, 1H), 8.45 (d, 1H), 9.26 (s, 1H).

Step B Preparation of 5-(2R)-2-oxiranyl-2-(trifluoromethyl)pyridine

To a solution of 2-chloro-1-[6-(trifluoromethyl)-3-pyridinyl]ethanone (i.e. the crude product obtained in Step A, 22 g) in acetonitrile (200 mL) was added a 5:2 formic acid/triethylamine mixture (19.6 g), and [N-(1[N-[(1S,2S)-2-(amino-κN)-1,2-diphenylethyl]-4-methylbenzenesulfonamidato-κN]chloro[(1,2,3,4,5,6-η)-1,3,5-trimethylbenzene]-ruthenium (CAS Registry No. 174813-81-1, 500 mg, 0.8 mmol). The resulting mixture was stirred at room temperature for 15 h during which time the progress was monitored by HPLC until less than 1% of the ethanone remained. To the reaction mixture was added 4 N aqueous sodium hydroxide (100 mL), and stirred for 2 h, the organic layer was separated and concentrated under reduced pressure to provide a brown oil, which was purified by column chromatography to provide the title compound as a light yellow oil (13.7 g).

$^1$H NMR δ 2.82 (dd, 1H), 3.26 (dd, 1H), 3.99 (m, 1H), 7.68 (d, 1H), 7.74 (d, 1H), 8.70 (s, 1H).

Step C Preparation of (βS)-β-chloro-N-methyl-N-(phenylmethyl)-6-(trifluoromethyl)-3-pyridineethanamine The mixture of 5-(2R)-2-oxiranyl-2-(trifluoromethyl) pyridine (i.e. the product obtained in Step B) (13.5 g, 71 mmol) and N-methyl-benzenemethanamine (9.0 g, 74 mmol) was stirred at 100° C. for 3 h during which time the progress was monitored by HPLC. After cooling to room temperature, dichloromethane (200 mL) was added, and the mixture was cooled in an ice bath to 10° C., then thionyl chloride (10.2 g, 86 mmol) was added over 30 min. The ice bath was removed, and the reaction mixture was stirred at room temperature (23° C.) for 2 h. The yellow solution was poured into ice-water (200 mL), the organic layer was separated, washed with saturated aqueous sodium bicarbonate solution, dried over MgSO$_4$, filtered and concentrated under reduced pressure to provide the title compound (14 g) as a light brown oil.

$^1$H NMR δ 2.33 (s, 3H), 2.95 (m, 2H), 3.45 (d, 1H), 3.58 (d, 1H), 4.88 (t, 1H), 7.05 (m, 2H), 7.21-7.23 (m, 3H), 7.60 (d, 1H), 7.72 (d, 1H), 8.60 (s, 1H).

Step D Preparation of 1,3-dimethyl 2-[(1S)-2-[methyl(phenylmethyl)amino]-1-[6-(trifluoromethyl)-3-pyridinyl]ethyl]propanedioate To a solution of (βS)-β-chloro-N-methyl-N-(phenylmethyl)-6-(trifluoromethyl)-3-pyridineethanamine (i.e. the product obtained in Step C) (14 g crude light brown oil from previous step) in acetonitrile (250 mL) added sodium dimethyl malonate (16 g, 104 mmol, freshly prepared from sodium hydride and dimethyl malonate in tetrahydrofuran) at ambient temperature, and stirred at 25° C. for 24 h. The mixture was diluted with saturated aqueous ammonium chloride (100 mL), then extracted with ethyl acetate (200 mL), the organic layer was separated and concentrated under reduced pressure to yield light yellow oil. The crude oil was purified by column chromatography to provide the title product (29 g) as a light yellow solid.

$^1$H NMR δ 2.22 (s, 3H), 2.60 (dd, 1H), 2.68 (dd, 1H), 3.36 (d, 1H), 3.49 (s, 3H), 3.54 (d, 1H), 3.74 (s, 3H), 3.75-3.78 (m, 2H), 7.04-7.06 (m, 2H), 7.21-7.24 (m, 3H), 7.55 (d, 1H), 7.60 (d, 1H), 8.52 (s, 1H).

Step E Preparation of methyl (3R,4S)-1-methyl-2-oxo-4-[6-(trifluoromethyl)-3-pyridinyl]-3-pyrrolidinecarboxylate To a 500 mL Parr shaker was added 1,3-dimethyl 2-[(1S)-2-[methyl(phenylmethyl)amino]-1-[6-(trifluoromethyl)-3-pyridinyl]ethyl]propanedioate (i.e. the product obtained in Step D) (14 g 33 mmol), methanol (80 mL) and 5% palladium on carbon (2.3 g). The mixture was degassed by 5 cycles of pressuring with hydrogen to 345 kPa (50 psi) and releasing, then shaken for 6 h under hydrogen 345 kPa (50 psi) at 24° C. The mixture was filtered to remove palladium on carbon then the filtrate was concentrated under reduced pressure and purified by column chromatography on silica gel to provide the title product as a white solid (7.2 g, 77% e.e.).

$^1$H NMR δ 2.97 (s, 3H), 3.44 (dd, 1H), 3.57 (d, 1H), 3.81 (s, 3H), 3.87 (dd, 1H), 4.13 (q, 1H), 7.69 (d, 1H), 7.75 (d, 1H), 7.86 (s, 1H).

Step F Preparation of (3S,4S)-N-(2,3-difluorophenyl)-1-methyl-2-oxo-4-[6-(trifluoromethyl)-3-pyridinyl]-3-pyrrolidinecarboxamide A mixture of methyl (3R,4S)-1-methyl-2-oxo-4-[6-(trifluoromethyl)-3-pyridinyl]-3-pyrrolidinecarboxylate (i.e. the product obtained in Step E) (9.3 g, 31 mmol, 77% e.e.) and 2,3-difluoroaniline (18 g, 142 mmol) was heated at 135° C. for 10 h, the progress of reaction was monitored by HPLC until the conversion is greater than 98%. The mixture was cooled to ambient temperature and the resulting solidified residue was slurried with dichloromethane (50 mL) and n-chlorobutane (50 mL) at ambient temperature for 30 min, the slurry was filtered, dried under suction to provide the title product (7.1 g, 98% e.e.) as an off-white solid.

$^1$H NMR δ 3.04 (s, 3H), 3.53 (dd, 1H), 3.64 (d, 1H), 3.83 (dd, 1H), 4.19 (q, 1H), 6.87-6.93 (m, 1H), 7.00-7.05 (m, 1H), 7.71 (d, 1H), 7.90 (d, 1H), 7.95 (t, 1H), 8.79 (s, 1H), 10.0 (s, 1H).

Synthesis Example 5

Preparation of methyl (3S,4S)-4-[2-(difluoromethoxy)-6-methyl-4-pyridinyl]-N-(2,3-difluorophenyl)-1-methyl-2-oxo-3-pyrrolidinecarboxamide Step A: Preparation of 2-(difluoromethoxy)-4-(1-ethoxyethenyl)-6-methyl-pyridine To stirring anhydrous N,N-dimethylformamide (660 mL) degassed with nitrogen, were added tributyl(1-ethoxyvinyl)tin (73 g, 202 mmol), and tetrakis(triphenylphosphine) palladium(0) (9.7 g, 8.39 mmol), followed by 4-bromo-2-(difluoromethoxy)-6-methyl-pyridine (40 g, 168 mmol). The resulting reaction mixture was heated with stirring at 80° C. After 40 h, an additional amount of palladium catalyst (2.0 g, 1.7 mmol) was introduced and heating was continued until reaction was determined to be complete (57 h). Once cooled to ambient temperature, the reaction mixture was poured into a stirred solution of potassium fluoride (122 g, 2.1 mol) in water (0.9 L), and the resulting suspension was filtered through Celite® diatomaceaous earth filter aid. The filter cake was washed thoroughly with diethyl ether, and the filtrate was poured into a separatory funnel. The aqueous layer was separated and extracted with a mixture of diethyl ether/hexanes (1:1). The combined organic layers were washed with water, brine, dried over MgSO$_4$, and filtered. Concentrated the filtrate to ¼ volume under reduced pressure, in a low temperature bath (14° C.). The remaining crude material was purified by silica gel chromatography (20:1 to 8:1 hexanes in ethyl acetate) to provide the title compound as an oil (35.8 g).

$^1$H NMR δ 1.43 (t, 3H), 2.47 (s, 3H), 3.91 (q, 2H), 4.35 (d, 1H), 4.80 (d, 1H), 6.92 (s, 1H), 7.15 (s, 1H), 7.51 (t, 1H).

Step B: Preparation of 2-bromo-1-[2-(difluoromethoxy)-6-methyl-4-pyridinyl]ethanone To 2-(difluoromethoxy)-4-(1-ethoxyethenyl)-6-methyl-pyridine (i.e. the product obtained in Step A) (35 g, 0.153 mol) stirring in tetrahydrofuran (1.05 L) and water (72 mL), was added N-bromosuccinimide (32.7 g, 0.184 mol). The reaction mixture was allowed to stir at ambient temperature 1 h, until completion. The reaction mixture was concentrated under reduced pressure, and the remaining aqueous mixture was partitioned between dichloromethane (80 mL) and water (50 mL). The aqueous layer was extracted with dichloromethane, and the combined organic layers were washed with aqueous sodium bisulfite solution, water, brine, and dried over MgSO$_4$ and filtered. The filtrate was concentrated under reduced pressure, and the residual crude oil was purified by silica gel chromatography to provide the title product as an off-white solid (38 g).

$^1$H NMR δ 2.56 (s, 3H), 4.37 (s, 2H), 7.15 (s, 1H), 7.40 (s, 1H), 7.52 (t, 1H).

Step C: Preparation 2-(difluoromethoxy)-6-methyl-4-(2R)-2-oxiranylpyridine

To a stirring solution of 2-bromo-1-[2-(difluoromethoxy)-6-methyl-4-pyridinyl]ethanone (i.e. the product obtained in Step B) (15.0 g, 53.56 mmol) in acetonitrile (anhydrous, 265 mL), was added formic acid/triethylamine complex (5:2, 9.74 g), followed by [N-(1[N-[(1S,2S)-2-(amino-κN)-1,2-diphenylethyl]-4-methylbenzenesulfonamidato-κN]chloro [(1,2,3,4,5,6-η)-1,3,5-trimethylbenzene]-ruthenium (CAS Registry No. 174813-81-1, 123 mg, 0.198 mmol) (1.13 mg, 1.823 mmol). The reaction mixture was stirred at ambient temperature. The reaction was completed in 10 min. (The enantiomeric excess of this intermediate 2-bromo-1-(2-difluoromethoxy-6-methyl-pyridin-4-yl)-ethanol, was determined to be 93%.) The reaction mixture was cooled to 10° C. Sodium hydroxide (54 mL, 4 N in H$_2$O) was added dropwise over 5 min, maintaining the reaction temperature at 10° C. The resulting mixture was stirred at room temperature for 50 min. The layers were separated. The aqueous layer was extracted with diethyl ether. The organic layers were combined, washed with brine, dried over MgSO$_4$ and filtered. Concentrated the resulting solution under reduced pressure provided the title product as a dark oil used in the next step (7.5 g).

$^1$H NMR δ 2.45 (s, 3H), 2.73 (dd, 1H), 3.16 (dd, 1H), 3.80 (dd, 1H), 6.62 (s, 1H), 6.85 (s, 1H), 7.49 (t, 1H).

Step D: Preparation of (βS)-β-chloro-2-(difluoromethoxy)-N,6-dimethyl-N-(phenylmethyl)-4-pyridineethanamine A mixture of 2-(difluoromethoxy)-6-methyl-4-(2R)-2-oxiranylpyridine (i.e. the product obtained in Step C) (25 g, 0.124 mol) and N-methyl-benzenemethanamine (15.76 g, 0.13 mol) in a round bottom flask equipped with a cool water condenser was warmed to 100° C. for 1 h with stirring. The mixture was cooled to ambient temperature and dichloromethane (250 mL) was added. This solution was cooled to −5° C. and thionyl chloride (18 g, 0.151 mol, diluted in 50 mL dichloromethane) was added at such a rate to keep the reaction temperature below 5° C. After the addition, the reaction mixture was further stirred at room temperature for 13 h and was added into water with caution. The mixture was adjusted to pH ~8 with sodium bicarbonate aqueous solution. The aqueous layer was separated and extracted with dichloromethane twice. The combined organic portions were dried over MgSO$_4$, filtered, and concentrated under reduced pressure to provide the title product as an oil (38 g), which was used directly in the next step.

$^1$H NMR δ 2.31 (s, 3H), 2.43 (s, 3H), 2.89 (d, 2H), 3.48 (d, 1H), 3.59 (d, 1H), 6.60 (s, 1H), 6.81 (s, 1H), 7.14-7.27 (m, 5H), 7.50 (t, 1H).

Step E: Preparation of 1,3-dimethyl 2-[(1S)-1-[2-(difluoromethoxy)-6-methyl-4-pyridinyl]-2-[methyl(phenylmethyl)amino]ethyl]propanedioate To a solution of (βS)-β-chloro-2-(difluoromethoxy)-N,6-dimethyl-N-(phenylmethyl)-4-pyridineethanamine (i.e. the crude brown oil obtained in Step D) (54 g, 158 mmol) in acetonitrile (750 mL) was added sodium dimethyl malonate (34 g, 221 mmol, freshly prepared from sodium hydride and dimethyl malonate and tetrahydrofuran) at ambient temperature, and stirred at ambient temperature for 24 h. The mixture was diluted with saturated NH$_4$Cl (aq) (500 mL), then extracted with ethyl acetate (750 mL). The organic layer was separated and concentrated under reduced pressure to yield a light yellow oil. The crude oil was purified by column chromatography to provide title product (56 g, 80% e.e.) as a light yellow oil contaminated with dimethyl malonate. Methanol (500 mL) was added and stirred at ambient temperature for 20 h. A white solid was removed by filtration (which consisted of a low % e.e. product of the title compound). The filtrate was concentrated under reduced pressure to provide the title product (47 g, 94% e.e.) as light yellow oil which also contained dimethyl malonate.

$^1$H NMR δ 2.19 (s, 3H), 2.41 (s, 3H), 2.51-2.60 (m, 2H), 3.38 (d, 1H), 3.53 (s, 3H), 3.54 (d, 1H), 3.64-3.69 (m, 2H), 3.73 (s, 3H), 6.45 (s, 1H), 6.71 (s, 1H), 7.13-7.14 (m, 2H), 7.23-7.28 (m, 3H), 7.48 (t, 1H).

Step F: Preparation of methyl (3R,4S)-4-[2-(difluoromethoxy)-6-methyl-4-pyridinyl]-1-methyl-2-oxo-3-pyrrolidinecarboxylate To a 500 mL Parr shaker added 1,3-dimethyl 2-[(1S)-1-[2-(difluoromethoxy)-6-methyl-4-pyridinyl]-2-[methyl(phenylmethyl)amino]ethyl]propanedioate (i.e. the product obtained in Step E) (16 g, 36.7 mmol), methanol (100 mL) and 10% palladium on carbon (8 g). The mixture was degassed by 3 cycles of nitrogen-hydrogen, then shaken for 2 h under hydrogen 345 kPa (50 psi) at ambient temperature. The mixture was filtered to remove palladium(0) on carbon, the filtrate was concentrated under reduced pressure, and purified by column chromatography on silica gel to provide the title product as a white solid (9.9 g).

$^1$H NMR δ 2.46 (s, 3H), 2.95 (s, 3H), 3.38 (dd, 1H), 3.53 (d, 1H), 3.81 (s, 3H), 3.80-3.82 (m, 1H), 3.95 (dd, 1H), 6.55 (s, 1H), 6.79 (s, 1H), 7.50 (t, 1H).

Step G: Preparation of methyl (3S,4S)-4-[2-(difluoromethoxy)-6-methyl-4-pyridinyl]-N-(2,3-difluorophenyl)-1-methyl-2-oxo-3-pyrrolidinecarboxamide A mixture of methyl (3R,4S)-4-[2-(difluoromethoxy)-6-methyl-4-pyridinyl]-1-methyl-2-oxo-3-pyrrolidinecarboxylate (i.e. the product obtained in Step F) (29 g, 92.2 mmol), 2,3-difluoroaniline (15.3 g, 118 mmol) and xylene (300 mL) was heated at 142° C. for 16 h, the progress of reaction was monitored by NMR until the conversion was greater than 98%. After cooling to ambient temperature, the mixture was concentrated to 50 mL under reduced pressure, then purified by column chromatography on silica gel to provide the title product (32 g, 94% e.e.) as an off-white solid.

$^1$H NMR δ 2.48 (s, 3H), 3.01 (s, 3H), 3.43 (dd, 1H), 3.62 (d, 1H), 3.78 (dd, 1H), 4.06 (dd, 1H), 6.69 (s, 1H), 6.88-6.93 (m, 1H), 6.95 (s, 1H), 7.01-7.05 (m, 1H), 7.51 (t, 1H), 7.97-8.01 (m, 1H), 10.03 (s, 1H).

What is claimed is:

1. A process for preparing a compound of Formula II-B

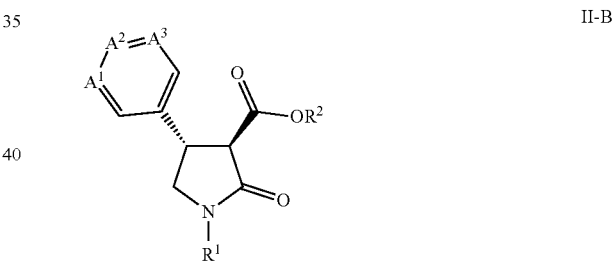

II-B wherein
$A^1$ is CCF$_3$, $A^2$ is CH and $A^3$ is CH; or
$A^1$ is CH, $A^2$ is CCF$_3$ and $A^3$ is CH; or
$A^1$ is N, $A^2$ is CCF$_3$ and $A^3$ is CH; or
$A^1$ is CCH$_3$, $A^2$ is N and $A^3$ is COCHF$_2$;
$R^1$ is C$_1$-C$_4$ alkyl; and
$R^2$ is C$_1$-C$_4$ alkyl
comprising reducing a compound of Formula IV

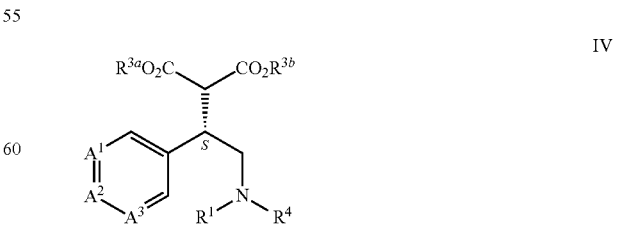

IV wherein
$A^1$ is CCF$_3$, $A^2$ is CH and $A^3$ is CH; or
$A^1$ is CH, $A^2$ is CCF$_3$ and $A^3$ is CH; or $A^1$ is N, $A^2$ is CCF$_3$ and $A^3$ is CH; or
$A^1$ is CCH$_3$, $A^2$ is N and $A^3$ is COCHF$_2$;
$R^1$ is C$_1$-C$_4$ alkyl;
each $R^{3a}$ and $R^{3b}$ is independently C$_1$-C$_4$ alkyl; and
$R^4$ is substituted or unsubstituted benzyl
with a reducing agent.

2. The process of claim 1 wherein
in the compound of Formula II-B
$R^1$ is methyl, ethyl or propyl; and
$R^2$ is methyl, ethyl, n-propyl, i-propyl, n-butyl or t-butyl
comprising reducing a compound of Formula IV
wherein
$R^1$ is methyl, ethyl or propyl;
each $R^{3a}$ and $R^{3b}$ is independently methyl or ethyl; and
$R^4$ is unsubstituted benzyl
wherein the reducing agent comprises a catalyst.

3. A process for preparing a compound of Formula IV

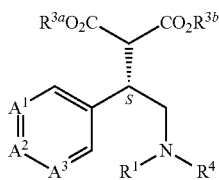

IV wherein
$A^1$ is CCF$_3$, $A^2$ is CH and $A^3$ is CH; or
$A^1$ is CH, $A^2$ is CCF$_3$ and $A^3$ is CH; or
$A^1$ is N, $A^2$ is CCF$_3$ and $A^3$ is CH; or
$A^1$ is CCH$_3$, $A^2$ is N and $A^3$ is COCHF$_2$;
$R^1$ is C$_1$-C$_4$ alkyl;
each $R^{3a}$ and $R^{3b}$ is independently C$_1$-C$_4$ alkyl; and
$R^4$ is substituted or unsubstituted benzyl
comprising reacting a compound of Formula V or a salt thereof

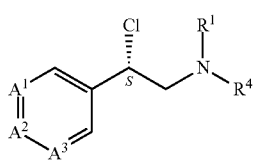

V wherein
$A^1$ is CCF$_3$, $A^2$ is CH and $A^3$ is CH; or
$A^1$ is CH, $A^2$ is CCF$_3$ and $A^3$ is CH; or
$A^1$ is N, $A^2$ is CCF$_3$ and $A^3$ is CH; or
$A^1$ is CCH$_3$, $A^2$ is N and $A^3$ is COCHF$_2$;
$R^1$ is C$_1$-C$_4$ alkyl; and
$R^4$ is substituted or unsubstituted benzyl with a di-(C$_1$-C$_4$ alkyl) malonate, or a salt thereof.

4. The process of claim 3 wherein in the compound of Formula IV
$R^1$ is methyl, ethyl or propyl;
each $R^{3a}$ and $R^{3b}$ is independently methyl, ethyl or propyl; and
$R^4$ is unsubstituted benzyl comprising reacting a compound of Formula V or a salt thereof wherein
$R^1$ is methyl, ethyl or propyl; and
$R^4$ is unsubstituted benzyl with a di-(C$_1$-C$_4$ alkyl) malonate or a salt thereof selected from the group consisting of dimethyl malonate, diethyl malonate, diisopropyl malonate or di-n-propyl malonate or a sodium, lithium or potassium salt thereof.

5. A process for preparing a compound of Formula I

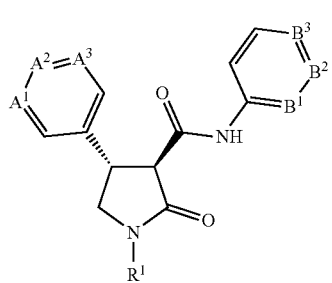

I wherein
$A^1$ is CCF$_3$, $A^2$ is CH and $A^3$ is CH; or
$A^1$ is CH, $A^2$ is CCF$_3$ and $A^3$ is CH; or
$A^1$ is N, $A^2$ is CCF$_3$ and $A^3$ is CH; or
$A^1$ is CCH$_3$, $A^2$ is N and $A^3$ is COCHF$_2$;
$R^1$ is C$_1$-C$_4$ alkyl;
$B^1$ is CF, $B^2$ is CH and $B^3$ is CH; or
$B^1$ is CF, $B^2$ is CF and $B^3$ is CH; or
$B^1$ is CF, $B^2$ is N and $B^3$ is CF comprising contacting a compound of Formula II-A

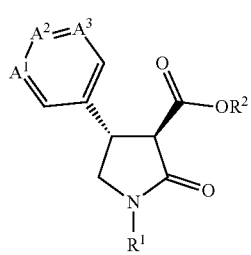

II-A wherein
$A^1$ is CCF$_3$, $A^2$ is CH and $A^3$ is CH; or
$A^1$ is CH, $A^2$ is CCF$_3$ and $A^3$ is CH; or
$A^1$ is N, $A^2$ is CCF$_3$ and $A^3$ is CH; or
$A^1$ is CCH$_3$, $A^2$ is N and $A^3$ is COCHF$_2$;
$R^1$ is C$_1$-C$_4$ alkyl; and
$R^2$ is H
with a compound of Formula VI

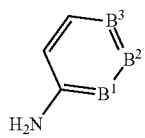

VI wherein
$B^1$ is CF, $B^2$ is CH and $B^3$ is CH; or
$B^1$ is CF, $B^2$ is CF and $B^3$ is CH; or
$B^1$ is CF, $B^2$ is N and $B^3$ is CF
wherein the compound of Formula II-A is prepared by a process comprising alkylating a compound of Formula III

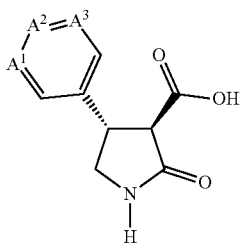

III wherein
A¹ is CCF₃, A² is CH and A³ is CH; or
A¹ is CH, A² is CCF₃ and A³ is CH; or
A¹ is N, A² is CCF₃ and A³ is CH; or
A¹ is CCH₃, A² is N and A³ is COCHF₂
with an alkylating agent.

6. The process of claim 5 wherein in the compound of Formula I
R¹ is methyl, ethyl or propyl;
comprising contacting a compound of Formula II-A
wherein
R¹ is methyl, ethyl or propyl
with a compound of Formula VI.

7. The process of claim 6 wherein a compound of Formula II-A is prepared using the process described in claim 5 comprising alkylating a compound of Formula III.

8. The process of claim 6 wherein a compound of Formula II-A is prepared by first hydrolyzing the compound of Formula II-B

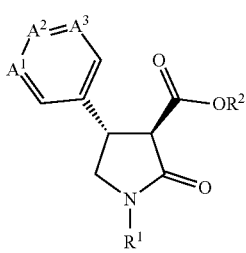

II-A wherein
A¹ is CCF₃, A² is CH and A³ is CH; or
A¹ is CH, A² is CCF₃ and A³ is CH; or
A¹ is N, A² is CCF₃ and A³ is CH; or
A¹ is CCH₃, A² is N and A³ is COCHF₂;
R¹ is C₁-C₄ alkyl; and
R² is C₁-C₄ alkyl.

9. A process for preparing a compound of Formula I

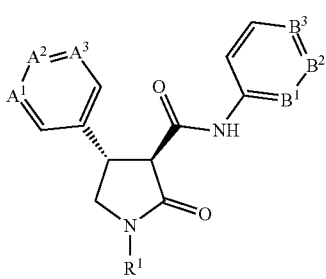

I wherein
A¹ is CCF₃, A² is CH and A³ is CH; or
A¹ is CH, A² is CCF₃ and A³ is CH; or
A¹ is N, A² is CCF₃ and A³ is CH; or
A¹ is CCH₃, A² is N and A³ is COCHF₂;
R¹ is C₁-C₄ alkyl;
B¹ is CF, B² is CH and B³ is CH; or
B¹ is CF, B² is CF and B³ is CH; or
B¹ is CF, B² is N and B³ is CF
comprising contacting a compound of Formula II-B

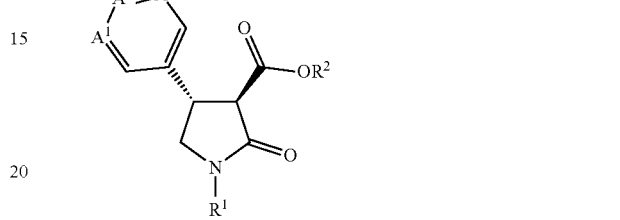

II-B wherein
A¹ is CCF₃, A² is CH and A³ is CH; or
A¹ is CH, A² is CCF₃ and A³ is CH; or
A¹ is N, A² is CCF₃ and A³ is CH; or
A¹ is CCH₃, A² is N and A³ is COCHF₂;
R¹ is C₁-C₄ alkyl; and
R² is C₁-C₄ alkyl
with a compound of Formula VI

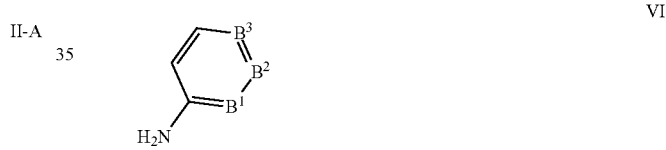

VI wherein
B¹ is CF, B² is CH and B³ is CH; or
B¹ is CF, B² is CF and B³ is CH; or
B¹ is CF, B² is N and B³ is CF
wherein the compound of Formula II-B is prepared by the process according to claim 1.

10. The process of claim 9 wherein
in the compound of Formula I
R¹ is methyl, ethyl or propyl
comprising contacting a compound of Formula II-B
wherein
R¹ is methyl, ethyl or propyl; and
R² is methyl, ethyl, n-propyl, i-propyl, n-butyl or t-butyl
with a compound of Formula VI.

11. The process of claim 9 wherein a compound of Formula II-B is prepared using the process described in claim 1 comprising reducing a compound of Formula IV

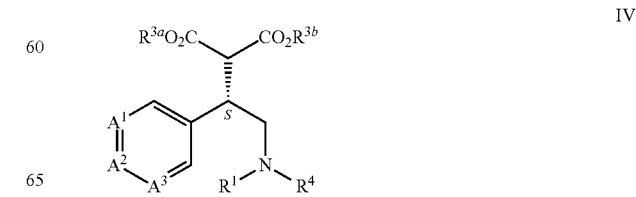

IV wherein
A$^1$ is CCF$_3$, A$^2$ is CH and A$^3$ is CH; or
A$^1$ is CH, A$^2$ is CCF$_3$ and A$^3$ is CH; or
A$^1$ is N, A$^2$ is CCF$_3$ and A$^3$ is CH; or
A$^1$ is CCH$_3$, A$^2$ is N and A$^3$ is COCHF$_2$;
R$^1$ is C$_1$-C$_4$ alkyl;
each R$^{3a}$ and R$^{3b}$ is independently C$_1$-C$_4$ alkyl; and
R$^4$ is substituted or unsubstituted benzyl with a reducing agent.

12. The process of claim 9 wherein a compound of Formula II-B is prepared using the process described in claim 1 comprising reducing a compound of Formula IV and the compound of Formula IV is prepared using the process as described claim 3 comprising reacting a compound of Formula V or a salt thereof with a di-(C$_1$-C$_4$ alkyl) malonate or a salt thereof.

* * * * *